(12) United States Patent
Stern

(10) Patent No.: US 6,413,255 B1
(45) Date of Patent: Jul. 2, 2002

(54) APPARATUS AND METHOD FOR TREATMENT OF TISSUE

(75) Inventor: Roger A. Stern, Cupertino, CA (US)

(73) Assignee: Thermage, Inc., Hayward, CA (US)

( * ) Notice: Subject to any disclaimer, the term of this patent is extended or adjusted under 35 U.S.C. 154(b) by 0 days.

(21) Appl. No.: 09/522,275

(22) Filed: Mar. 9, 2000

Related U.S. Application Data

(60) Provisional application No. 60/123,440, filed on Mar. 9, 1999.

(51) Int. Cl.⁷ .............................................. A61B 18/18
(52) U.S. Cl. ...................... 606/41; 607/101; 607/102; 607/108; 607/145
(58) Field of Search ...................... 606/41, 42, 50, 606/48, 39; 607/97–99, 101, 102, 109, 108, 103, 104, 139, 140, 148, 152, 105

(56) References Cited

U.S. PATENT DOCUMENTS 4,976,709 A * 12/1990 Sand
5,755,753 A * 5/1998 Knowlton ...................... 607/98
6,169,926 B1 * 1/2001 Baker ........................... 607/99
6,228,078 B1 * 5/2001 Eggers et al. .................. 606/32
6,277,116 B1 * 8/2001 Utely et al. .................. 607/102

FOREIGN PATENT DOCUMENTS

WO    WO 96/34568    3/1996    ........... A61B/17/36
WO    WO 99/08614    12/1998    ........... A61B/17/39

* cited by examiner

*Primary Examiner*—Linda C. M. Dvorak
*Assistant Examiner*—David M. Ruddy
(74) *Attorney, Agent, or Firm*—Wilson, Sonsini Goodrich & Rosati

(57) ABSTRACT

An apparatus to treat the skin includes a template having a tissue interface surface and an energy delivery device coupled to the template. The energy delivery device is configured to be coupled to a power source and has a variable resistance portion. A sensor is coupled to one of the template, the energy delivery device, the tissue interface surface or a power source coupled to the energy delivery device.

In another embodiment the variable resistance portion configured to reduce an electrode edge effect

60 Claims, 22 Drawing Sheets

Dielectrically Coated Electrode

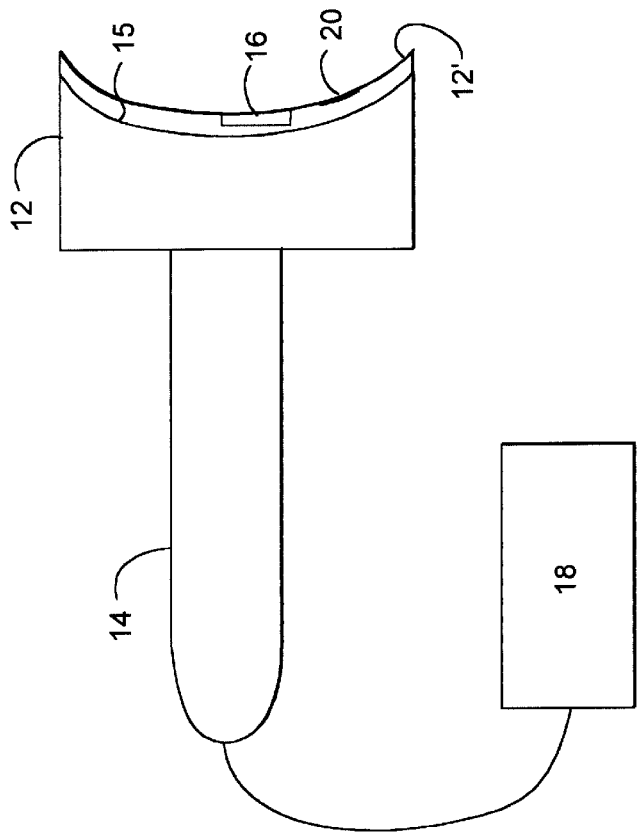
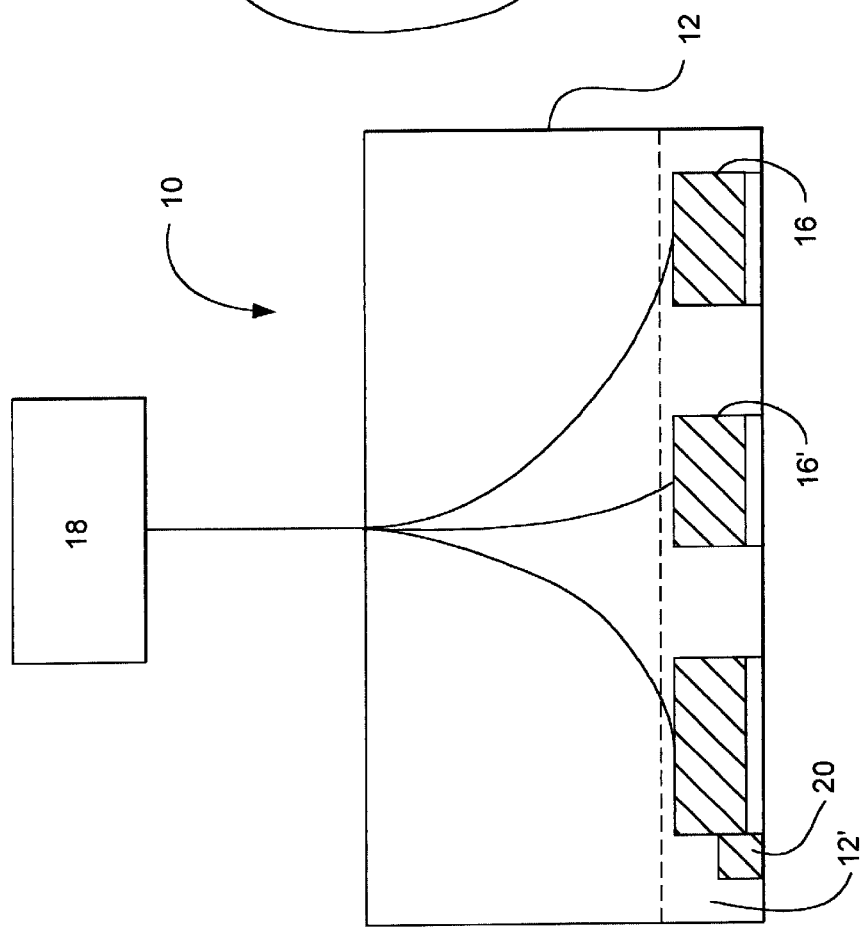
FIG. 2A
FIG. 1

Dielectrically Coated Electrode

Skin

APPARATUS AND METHOD FOR TREATMENT OF TISSUE

CROSS-REFERENCE TO RELATED APPLICATION

This application claims priority to U.S. application Ser. No. 60/123,440, filed Mar. 9, 1999, which is fully incorporated herein by reference.

FIELD OF THE INVENTION

This invention relates generally to a method and apparatus for treating tissue. More particularly, the invention relates to a method and apparatus for treating tissue using the controlled delivery of energy.

DESCRIPTION OF RELATED ART

The human skin is composed of two elements: the epidermis and the underlying dermis. The epidermis with the stratum corneum serves as a biological barrier to the environment. In the basilar layer of the epidermis, pigment-forming cells called melanocytes are present. They are the main determinants of skin color.

The underlying dermis provides the main structural support of the skin. It is composed mainly of an extracellular protein called collagen. Collagen is produced by fibroblasts and synthesized as a triple helix with three polypeptide chains that are connected with heat labile and heat stable chemical bonds. When collagen containing tissue is heated, alterations in the physical properties of this protein matrix occur at a characteristic temperature. The structural transition of collagen contraction occurs at a specific "shrinkage" temperature. The shrinkage and remodeling of the collagen matrix with heat is the basis for the technology.

Collagen crosslinks are either intramolecular (covalent or hydrogen bond) or intermolecular (covalent or ionic bonds). The thermal cleavage of intramolecular hydrogen crosslinks is a scalar process that is created by the balance between cleavage events and relaxation events (reforming of hydrogen bonds). No external force is required for this process to occur. As a result, intermolecular stress is created by the thermal cleavage of intramolecular hydrogen bonds. Essentially, the contraction of the tertiary structure of the molecule creates the initial intermolecular vector of contraction.

Collagen fibrils in a matrix exhibit a variety of spatial orientations. The matrix is lengthened if the sum of all vectors acts to distract the fibril. Contraction of the matrix is facilitated if the sum of all extrinsic vectors acts to shorten the fibril. Thermal disruption of intramolecular hydrogen bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming after lengthening or contraction of the fibril.

Hydrogen bond cleavage is a quantum mechanical event that requires a threshold of energy. The amount of (intramolecular) hydrogen bond cleavage required corresponds to the combined ionic and covalent intermolecular bond strengths within the collagen fibril. Until this threshold is reached, little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and nonpolar regions in the lengthened or contracted fibril.

Cleavage of collagen bonds also occurs at lower temperatures but at a lower rate. Low level thermal cleavage is frequently associated with relaxation phenomena in which bonds are reformed without a net change in molecular length. An external force that mechanically cleaves the fibril will reduce the probability of relaxation phenomena and provides a means to lengthen or contract the collagen matrix at lower temperatures while reducing the potential of surface ablation.

Soft tissue remodeling is a biophysical phenomenon that occurs at cellular and molecular levels. Molecular contraction or partial denaturization of collagen involves the application of an energy source, which destabilizes the longitudinal axis of the molecule by cleaving the heat labile bonds of the triple helix. As a result, stress is created to break the intermolecular bonds of the matrix. This is essentially an immediate extracellular process, whereas cellular contraction requires a lag period for the migration and multiplication of fibroblasts into the wound as provided by the wound healing sequence. In higher developed animal species, the wound healing response to injury involves an initial inflammatory process that subsequently leads to the deposition of scar tissue.

The initial inflammatory response consists of the infiltration by white blood cells or leukocytes that dispose of cellular debris. Seventy-two hours later, proliferation of fibroblasts at the injured site occurs. These cells differentiate into contractile myofibroblasts, which are the source of cellular soft tissue contraction. Following cellular contraction, collagen is laid down as a static supporting matrix in the tightened soft tissue structure. The deposition and subsequent remodeling of this nascent scar matrix provides the means to alter the consistency and geometry of soft tissue for aesthetic purposes.

In light of the preceding discussion, there are a number of dermatological procedures that lend themselves to treatments which deliver thermal energy to the skin and underlying tissue to cause a contraction of collagen, and/or initiate a would healing response. Such procedures include skin remodeling/resurfacing, wrinkle removal, and treatment of the sebaceous glands, hair follicles adipose tissue and spider veins. Currently available technologies that deliver thermal energy to the skin and underlying tissue include Radio Frequency (RF), optical (laser) and other forms of electromagnetic energy. However, these technologies have a number of technical limitations and clinical issues which limit the effectiveness of the treatment and/or preclude treatment altogether. These issues include the following: i) achieving a uniform thermal effect across a large area of tissue, ii) controlling the depth of the thermal effect to target selected tissue and prevent unwanted thermal damage to both target and nontarget tissue, iii) reducing adverse tissue effects such as burns, redness blistering, iv) replacing the practice of delivery energy/treatment in a patchwork fashion with a more continuous delivery of treatment (e.g. by a sliding or painting motion), v) improving access to difficult to reach areas of the skin surface and vi) reducing procedure time and number of patient visit; required to complete treatment, As will be discussed herein the current invention provides an apparatus for solving these and other limitations.

One of the key shortcomings of currently available RF technology for treating the skin is the edge effect phenomena. In general, when RF energy is being applied or delivered to tissue through an electrode which is in contact with that tissue, the current patterns concentrate around the edges of the electrode, sharp edges in particular. This effect is generally known as the edge effect. In the case of a circular disc electrode, the effect manifests as a higher current density around the perimeter of that circular disc and a relatively low current density in the center. For a square shaped electrode there is a high current density around the entire perimeter, and an even higher current density at the corners where there is a sharp edge.

Edge effects cause problems in treating the skin for several reasons. First they result in a nonuniform thermal effect over the electrode surface. In various treatments of the skin, it is important to have a uniform thermal effect over a relatively large surface area, particularly for dermatologic treatments. Large in this case being on the order of several square millimeters or even a square centimeter. In electrosurgical applications for cutting tissue, there typically is a point type applicator designed with the goal of getting a hot spot at that point for cutting or even coagulating tissue. However, this point design is undesirable for creating a reasonably gentle thermal effect over a large surface area. What is needed is an electrode design to deliver uniform thermal energy to skin and underlying tissue without hot spots.

A uniform thermal effect is particularly important when cooling is combined with heating in skin/tissue treatment procedure. As is discussed below, a non-uniform thermal pattern makes cooling of the skin difficult and hence the resulting treatment process as well. When heating the skin with RF energy, the tissue at the electrode surface tends to be warmest with a decrease in temperature moving deeper into the tissue. One approach to overcome this thermal gradient and create a thermal effect at a set distance away from the electrode is to cool the layers of skin that are in contact with the electrode. However, cooling of the skin is made difficult if there is a non-uniform heating pattern. If the skin is sufficiently cooled such that there are no burns at the corners of a square or rectangular electrode, or at the perimeter of a circular disc electrode, then there will probably be overcooling in the center and there won't be any significant thermal effect (i.e. tissue heating) under the center of the electrode. Contrarily, if the cooling effect is decreased to the point where there is a good thermal effect in the center of the electrode, then there probably will not be sufficient cooling to protect tissue in contact with the edges of the electrode. As a result of these limitations, in the typical application of a standard electrode there is usually an area of non-uniform treatment and/or burns on the skin surface. So uniformity of the heating pattern is very important. It is particularly important in applications treating skin where collagen containing layers are heated to produce a collagen contraction response for tightening of the skin. For this and related applications, if the collagen contraction and resulting skin tightening effect are non-uniform then a medically undesirable result may occur.

SUMMARY OF THE INVENTION

One embodiment of an apparatus for treating the skin includes a template having a tissue interface surface and an energy delivery device coupled to the template. The energy delivery device is configured to be coupled to a power source and has a variable resistance portion. A sensor is coupled to one of the template, the energy delivery device, the tissue interface surface or a power source coupled to the energy delivery device.

In another embodiment the variable resistance portion is configured to reduce an electrode edge effect.

BRIEF DESCRIPTION OF THE DRAWINGS

FIG. 1 is a lateral view of embodiments of the skin treatment apparatus illustrating components of the apparatus including the treatment template, energy delivery device and tissue interface surface.

FIG. 2a is a lateral view of an embodiment illustrating the use of a handpiece coupled to the treatment template.

DETAILED DESCRIPTION

Figure 2B:
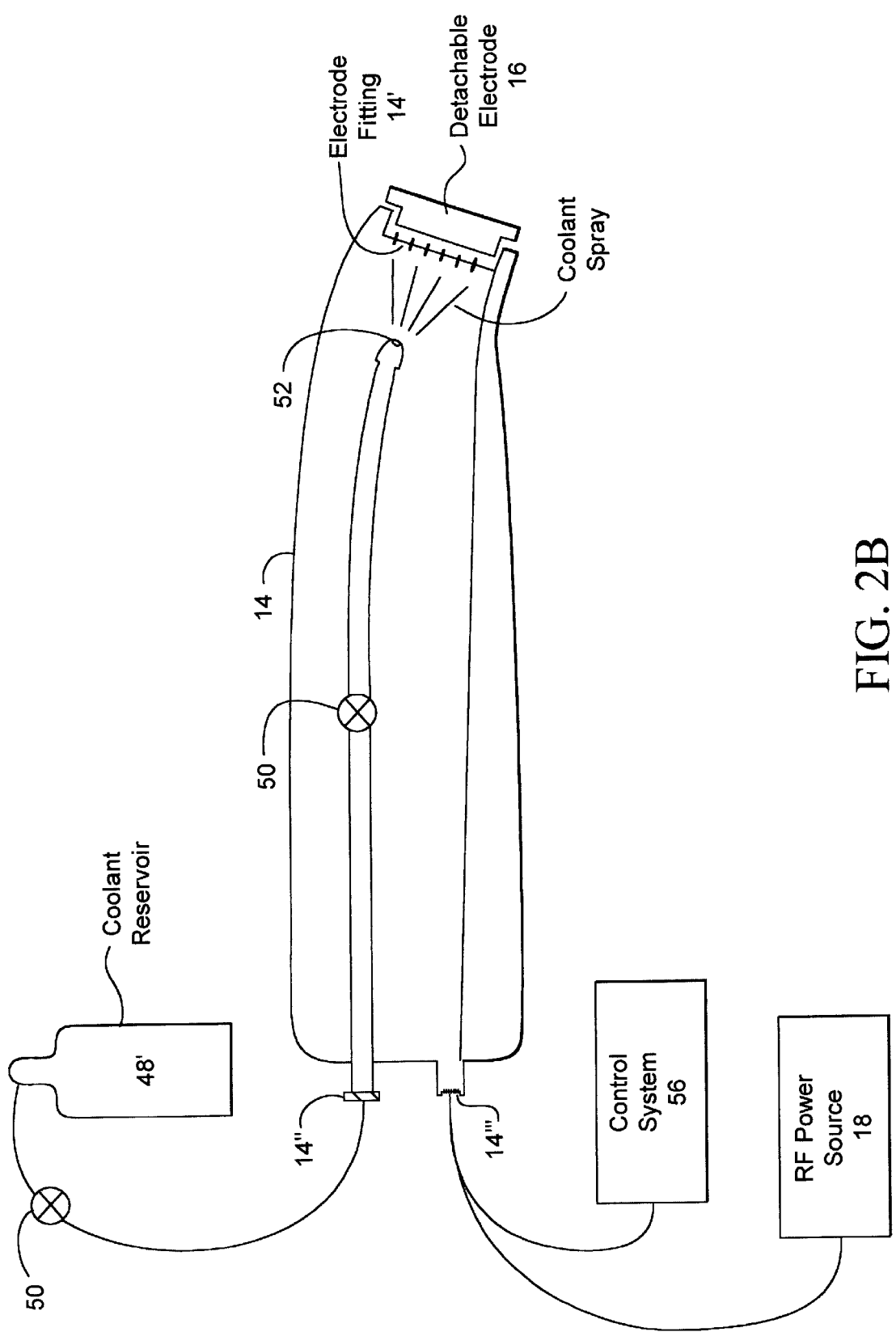
FIG. 2b is a lateral view of an embodiment illustrating the delivery of cooling fluid to the electrode using lumens, nozzles control valves and a control system. The figure also illustrates a detachable electrode.

The present invention provides an apparatus and methods for overcoming the problems, limitations and clinical issues with existing technology for treating the skin with radio frequency (RF), optical (laser) and other forms of electromagnetic energy. In various embodiments, the apparatus can be used to deliver thermal energy to modify tissue including, collagen containing tissue, in the epidermal, dermal and subcutaneous tissue layers including adipose tissue. The modification of the tissue includes modifying a physical feature of the tissue, a structure of the tissue or a physical property of the tissue. The modification can be achieved by delivering sufficient energy to cause collagen shrinkage, and/or a wound healing response including the deposition of new or nascent collagen. Various embodiments of the invention utilize novel electrode designs and cooling methods for providing a more uniform thermal effect in tissue at a selected depth while preventing or minimizing thermal damage to the skin surface and other non target tissue. The result is an improved aesthetic result/clinical outcome with an elimination/reduction in adverse effects and healing time.

In various embodiments the invention can be utilized for performing a number of treatments of the skin and underlying tissue including: dermal remodeling and tightening, wrinkle reduction, elastosis reduction sebaceous gland removal/deactivation, hair follicle removal, adipose tissue remodeling/removal and spider vein removal and combinations thereof.

Referring now to FIGS. 1 and 2a, one embodiment of an apparatus 10 to treat the skin includes a treatment template 12. In various embodiments, template 12 can be coupled to a handpiece 14. Also template 12 can include a receiving opening 15 adapted to receive and/or fit a body structure and make full or partial contact with the skin layer of that structure. One or more energy delivery devices 16 can be coupled to template 12 including receiving opening 15, and can form an energy delivery surface 12' on template 12. Energy delivery devices can have a tissue contacting layer 16' that delivers energy to the skin and/or underlying tissue. In various embodiments, energy can be delivered to the skin and/or underlying tissue, from energy delivery device 16, template energy delivery surface 12' or a combination of both.

Energy delivery device 16 is coupled to an energy source 18. Suitable energy sources 18 and energy delivery devices 16 that can be employed in one or more embodiments of the invention include: (i) a radio-frequency (RF) source coupled to an RF electrode, (ii) a coherent source of light coupled to an optical fiber, (iii) an incoherent light source coupled to an optical fiber, (iv) a heated fluid coupled to a fluid delivery device, (v) a cooled fluid coupled to a fluid delivery device, (vi) a cryogenic fluid, (vii) a microwave source providing energy from 915 MHz to 2.45 GHz and coupled to a microwave antenna, or (viii) an ultrasound power source coupled to an ultrasound emitter, wherein the ultrasound power source produces energy in the range of 300 KHZ to 3 GHz. For ease of discussion for the remainder of this specification, the energy source utilized is an RF source and energy delivery device 16 is one or more RF electrodes 16. However, all of the other herein mentioned energy sources and energy delivery devices are equally applicable to skin treatment apparatus 10.

A sensor 20 can be positioned at template energy delivery surface 12' or energy delivery device 16 to monitor temperature, impedance, pressure and the like. Suitable sensors 20 include impedance, pressure and thermal devices. Sensor 20 is used to control the delivery of energy and reduce the chance of cell necrosis at the surface of the skin as well as damage to underlying soft tissue structures. Sensor 20 is of conventional design, and includes but is not limited to thermistors, thermocouples, resistive wires, and the like. A suitable thermal sensor 20 includes a T type thermocouple with copper constantan, J type, E type, K type, fiber optics, thermistors, resistive wires, thermocouple IR detectors, and the like.

Referring now to FIG. 2b, in various embodiments handpiece 14 can be configured for multiple functions and can include one or more of the following: a fitting 14' for detachable electrodes, fluid and gas fittings 14", electrical fittings 14'" (e.g. Lemo connectors) for connection to power and control systems, a coolant valve 50 and a coolant spray nozzle 52. Handpiece 14 could be configured to be reusable, resterilized and compatible/interfacable with standard medical and electronic connectors and fittings known in the art.

Figure 3:
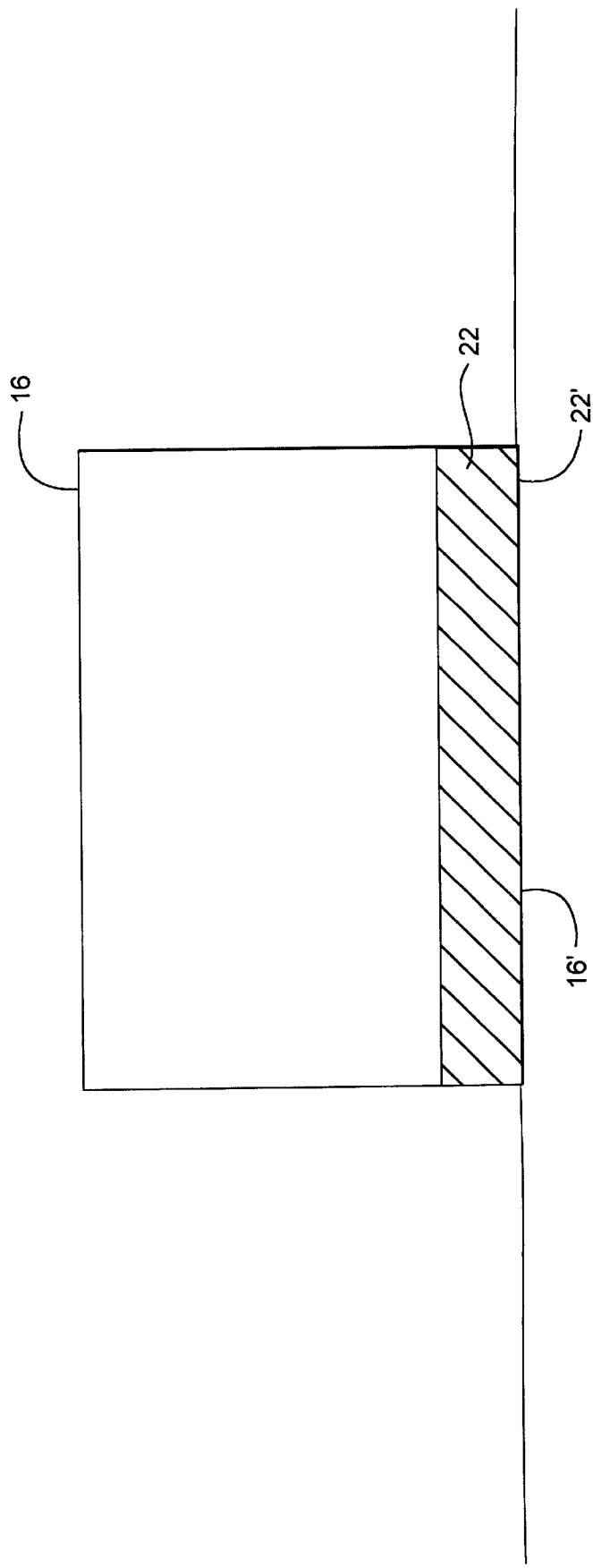
FIG. 3 is a lateral view of an embodiment illustrating the use of a variable resistance coating on the surface of the electrode

Referring now to FIG. 3, one embodiment for achieving uniform energy delivery from electrode 16 and minimizing edge effects involves coating all or a portion of the electrode with a variable resistance material 22 that has an electrical resistance that varies with temperature. In one embodiment, variable resistance material 22 is applied as a coating 22' on around tissue contact surface 16'.

Variable resistance material 22 can be selected to have a positive temperature coefficient of resistance (which means that its resistance increases with temperature.). These materials known as positive temperature coefficient semiconductors, can include ceramic semiconductive materials and polymers with embedded conductive particles. These and related materials, are well known in the art and are used for thermostats and other solid state temperature control devices. Such materials are available from the Raychem Corporation (Menlo Park, Calif.), an established supplier of positive temperature coefficient semiconductors. The use of such a positive temperature coefficient coating 22' prevents and/or reduces the formation of hot spots in the following manner. When hot spots begin to form on the edges of a coated electrode due to current concentration, the resistance of the coating 22' at the electrode edges goes up, resulting in a reduction in current flowing to and through these hot edges with an ultimate decrease in temperature of the edges and tissue in contact or near the edges.

Figure 4:
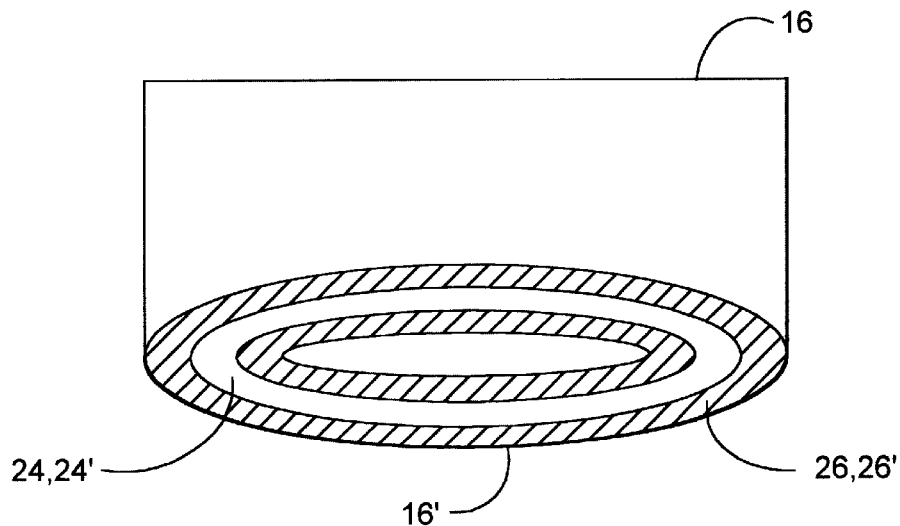
FIGS. 4 and 5 are perspective and cross-sectional views illustrating an embodiment of an electrode with rings of resistance material interposed between conductive material to generate a radial resistance gradient on the electrode surface.
Figure 5:
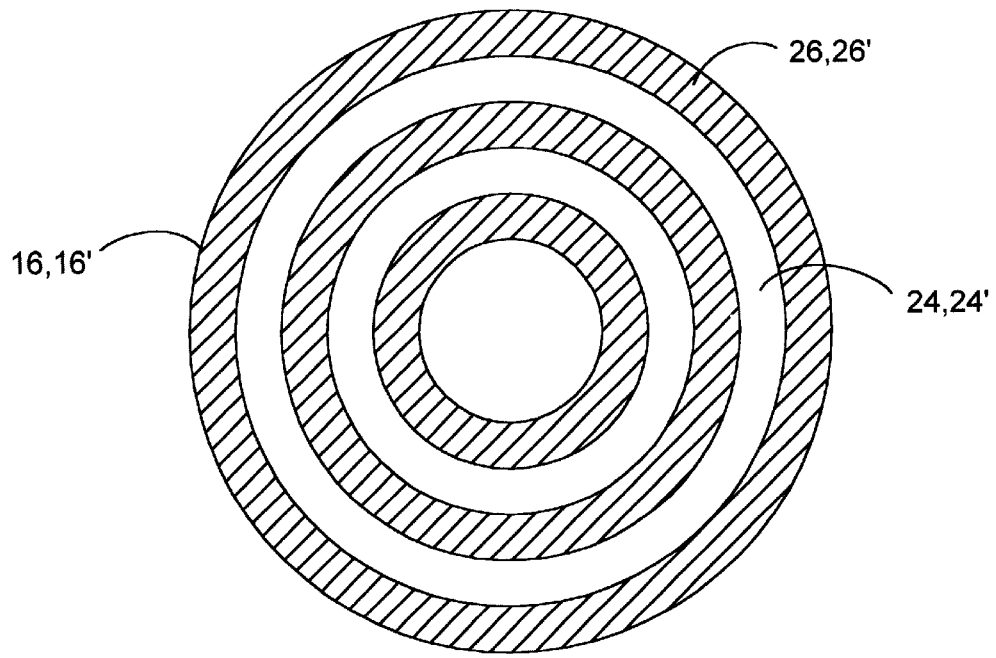

Another embodiment for obtaining a more uniform energy delivery and thermal effect in tissue is shown in FIGS. 4 and 5. In this embodiment electrode 16, comprises a circular disc, with a number of concentric conductive rings 24 of conductive material 24'. Interposed between the conductive rings 24, are resistance rings 26 made of material with a higher electrical resistance, called resistance material 26. The conductive and resistance rings 24 and 26 are configured such that there is a radial resistance gradient, with a higher electrical resistance at the outer edges of the electrode that decreases moving radially inwards. As a result, less current flow (and hence less heating) occurs through the edges and outer portions of the electrode compared to the more central electrode portions. Another embodiment for achieving a radial resistance gradient and minimizing hot spots, involves having thicker rings of resistant material in the outer electrode portions and progressively thinner resistance rings going toward the center of the electrode. Varying the resistance of the energy delivery surface 16' of the electrode, through the use of interposing rings of conductive and resistance material serves to increase the uniformity of current density across the electrode energy delivery surface 16', resulting in a more uniform delivery of energy to underlying tissue.

Figure 6A:
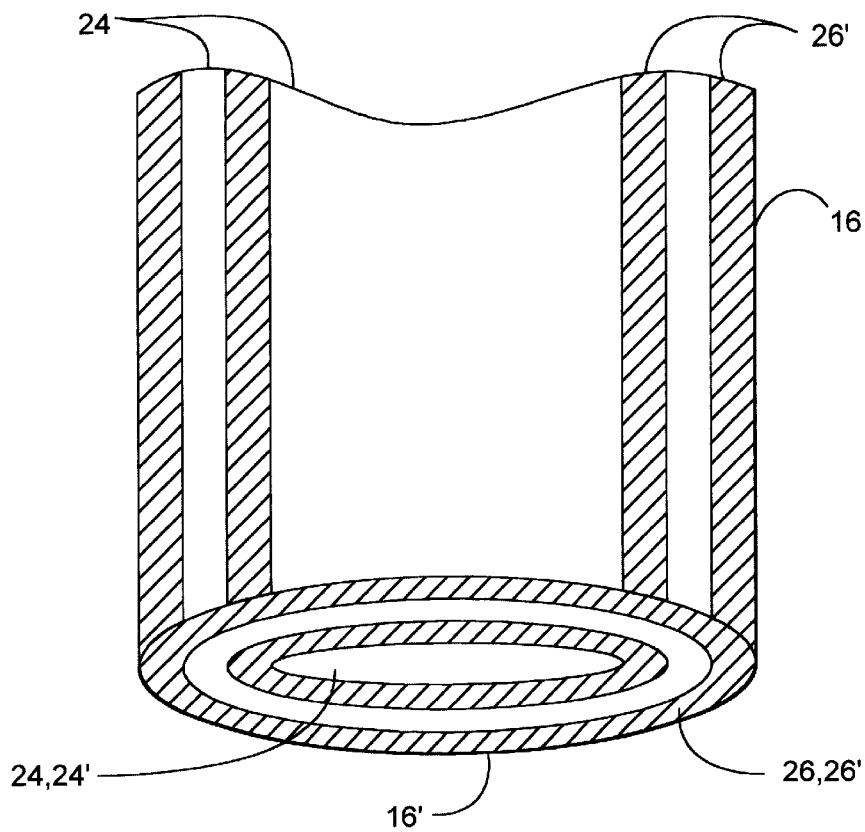
FIGS. 6A and 6B are perspective and cross-sectional views illustrating an embodiment of a cylindrical electrode with rings of resistance material interposed between conductive material, the resistance rings having increasing thickness moving in the outward radial direction.
Figure 6B:
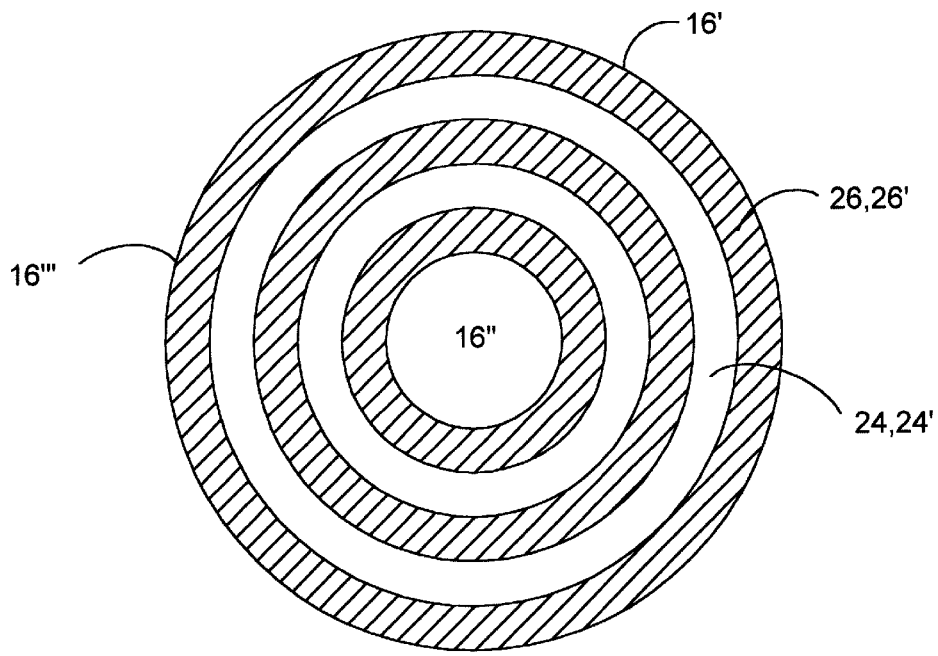

In related embodiments shown in FIGS. 6A and 6B, electrode 16 is cylindrically shaped and is fabricated such that it is made out of alternating layers of resistance material 26' and conductive material 24'. The bottom portion of the electrode is the tissue contacting surface 16' and hag s pattern of annular rings correlating to the layers of resistance and conductive material. Specifically, cylindrical electrode 16 is constructed such that the resistance rings 26 near the electrode center 16'' are thinner than those at the outer edges 16''' with a continuous increase in thickness moving in the outer radial direction. As result of this configuration, electrons flowing through electrode outer electrode edges 16''' must flow through more of resistance material 26 (e.g. encounter more resistance) than those flowing through the more central electrode portions 16''. Consequently, the net current flow on outer edges 16'''is less than in the more central electrode portion 16''. This ringed pattern can be made to a mathematical limit where the annular rings become thinner and thinner and closer and closer to one another such that there is almost a continuous tissue contacting surface of conducting material 24, but also with a continuous resistance element that causes the current flow to be less on the outer electrode edges 16''' than the inner portions 16''.

Figure 7:
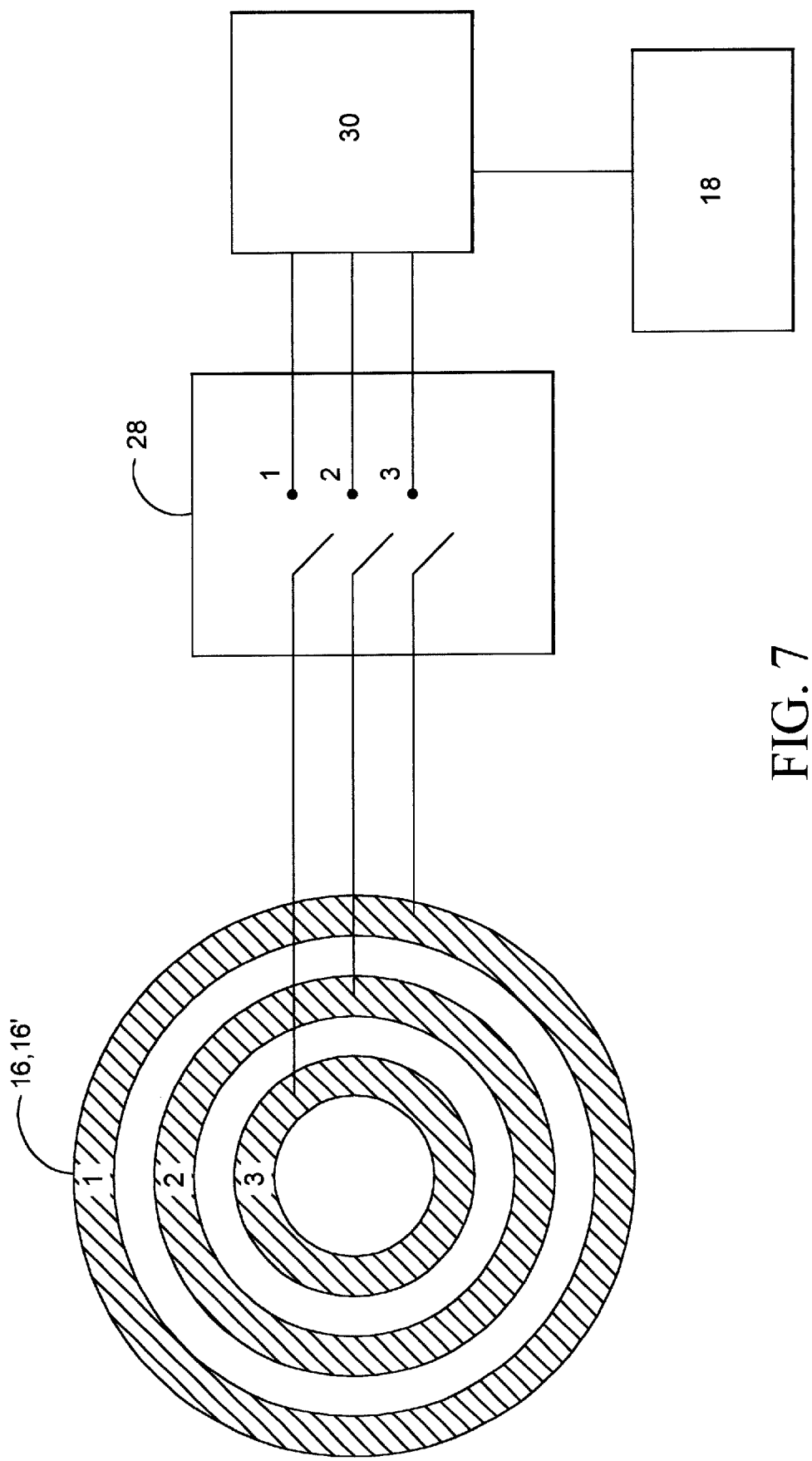
FIG. 7 is a cross-sectional/schematic view illustrating an embodiment of a ringed electrode coupled to a switching device, whereby duty cycle control of the conductive rings is used to achieve a more uniform current density across the surface of the electrode.

Referring now to FIG. 7, a related, but different, embodiment for reducing edges effects also involves dividing a circular disc electrode into annular conductive rings. However in this case, the flow of current through the rings is temporally controlled using a time sharing or duty cycle approach to turn on current flow to the inner and outer rings for fixed time periods. During a given duty cycle, RF current flow to the outer rings is turned on for the shortest periods of time with progressively longer on- times time moving inward in the radial direction. Although when the outer rings are turned on, they briefly have a higher current flow and are transiently hotter, this is compensated for by having them on for only a short time period and/or shorter than more centrally located electrode rings. Over time (e.g. on a time average basis) the result is a more uniform energy delivery to the tissue and hence thermal effect over the surface of the electrode. Adjacent rings can be switched on and off sequentially or in any other predetermined order or pattern. Also two or more rings can be turned on at the same time. The switching of rings can be controlled by a switching device/circuit 28, known in the art, electrically coupled to the rings.

Also, the rings can be multiplexed to energy source 18 using a multiplexing circuit 30 known in the art.

Figure 8:
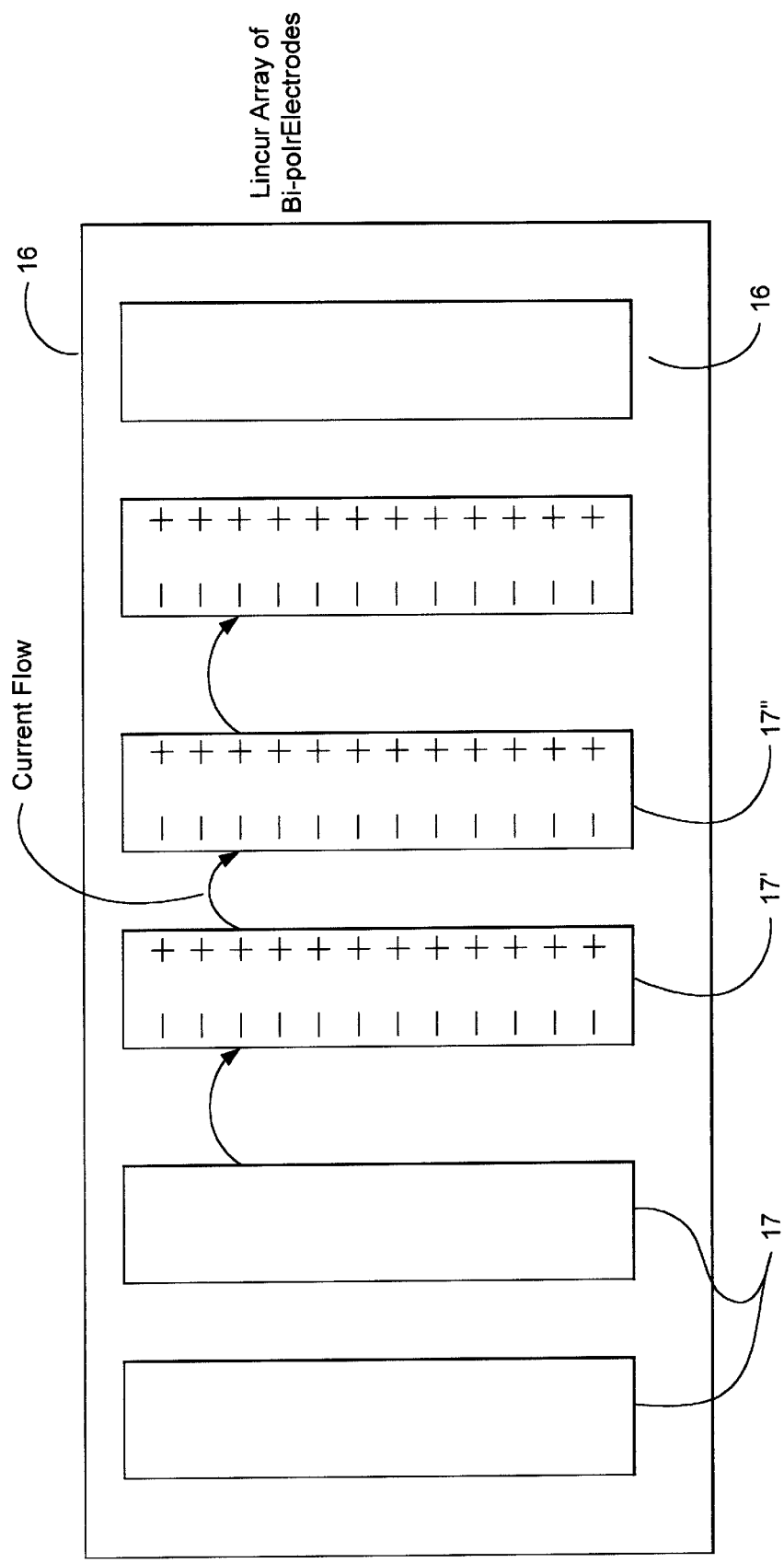
FIG. 8 is a cross-sectional/schematic view illustrating an embodiment of an energy delivery device having a linear array of bipolar electrodes.

In another embodiment shown in FIG. 8, the energy delivery device 16 can comprise a number of small rectangular shaped electrodes that are laid down (on a supporting surface, structure or substrate) and operated in a bi-polar fashion. In this embodiment, every pair of bars could be a bi-polar electrode pair 17 possibly with sequential switching between different pairs of bars to create a bi-polar effect.

Figure 9:
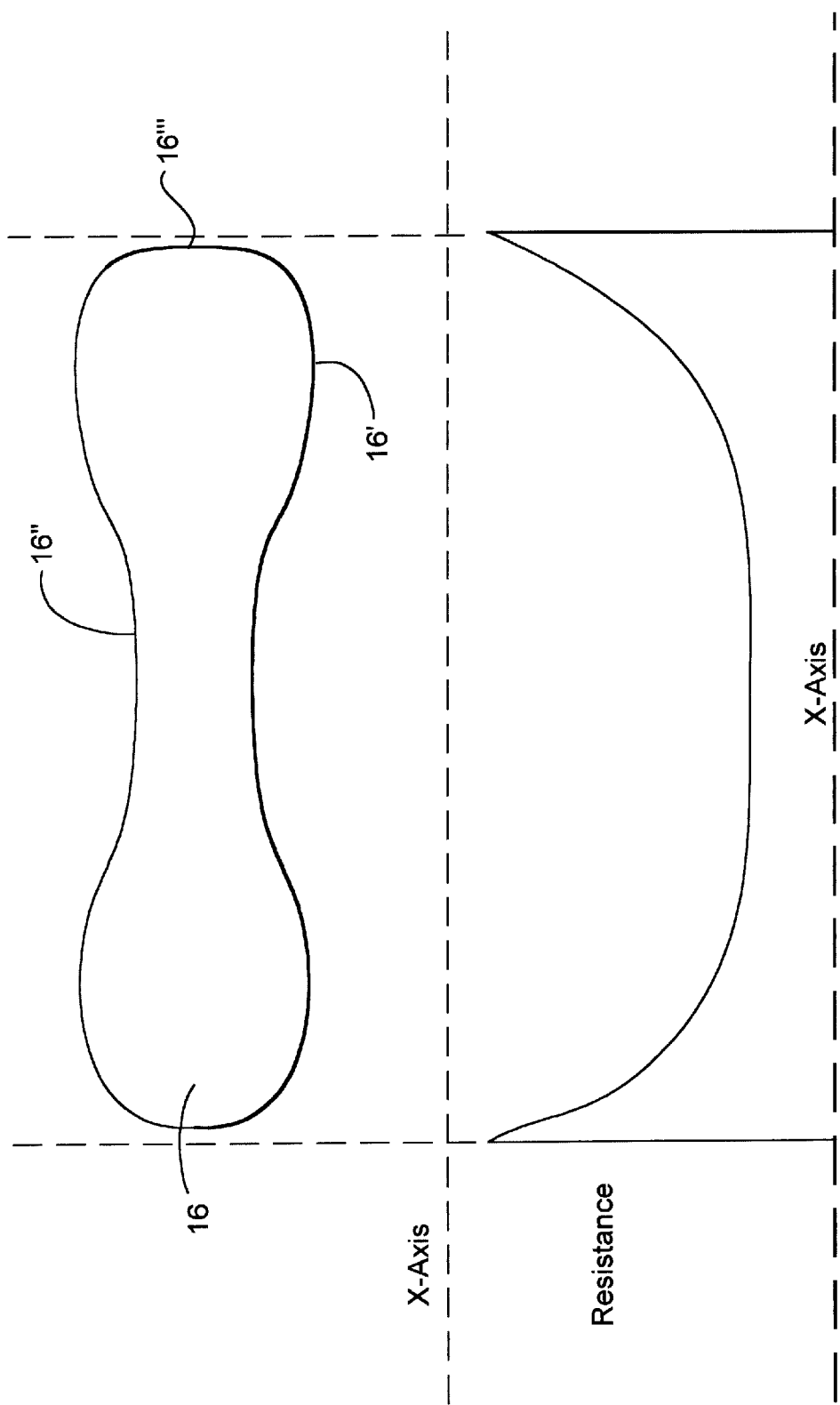
FIG. 9 is a cross-sectional/lateral view illustrating an embodiment of an electrode having a contoured thickness profile configured to produce a resistance gradient across the surface of the electrode to achieve a uniform current density.

In still other alternative embodiments for controlling electrode resistance and providing uniform energy delivery, electrode 16 can be fabricated such that it has a continuous variation in resistance moving in a radial or other direction. More specifically, the electrode can be configured to have a continuously decreasing resistance moving inwardly in the radial direction. One embodiment for achieving this result is shown in FIG. 9, which illustrates an electrode fabricated to have a tapered or otherwise contoured profile, thickest at the outer edges 16''' and thinner moving inward in the radial direction. By definition, the thicker sections of the electrode have increased resistance compared to the thinner sections (e.g. resistance is proportional to thickness). In a related, but distinct embodiment, a radial or other directional gradient in resistance can be achieved by doping, impregnating or coating the surface of the electrode with materials (known in the art) to increase its electrical resistance.

Figure 10A:
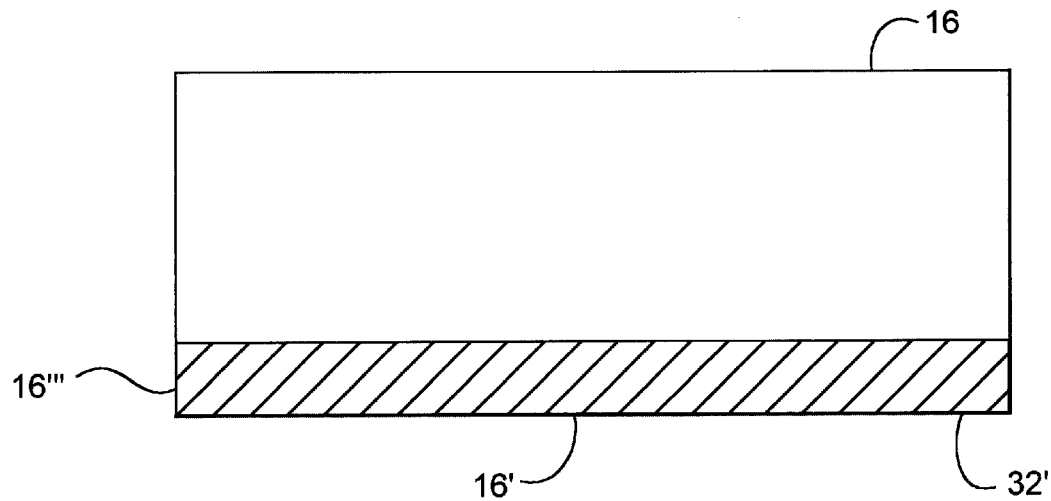
FIG. 10a is a lateral view of an embodiment of an electrode illustrating the use of a dielectric coating on the surface of the electrode to achieve a uniform current density.
Figure 10B:
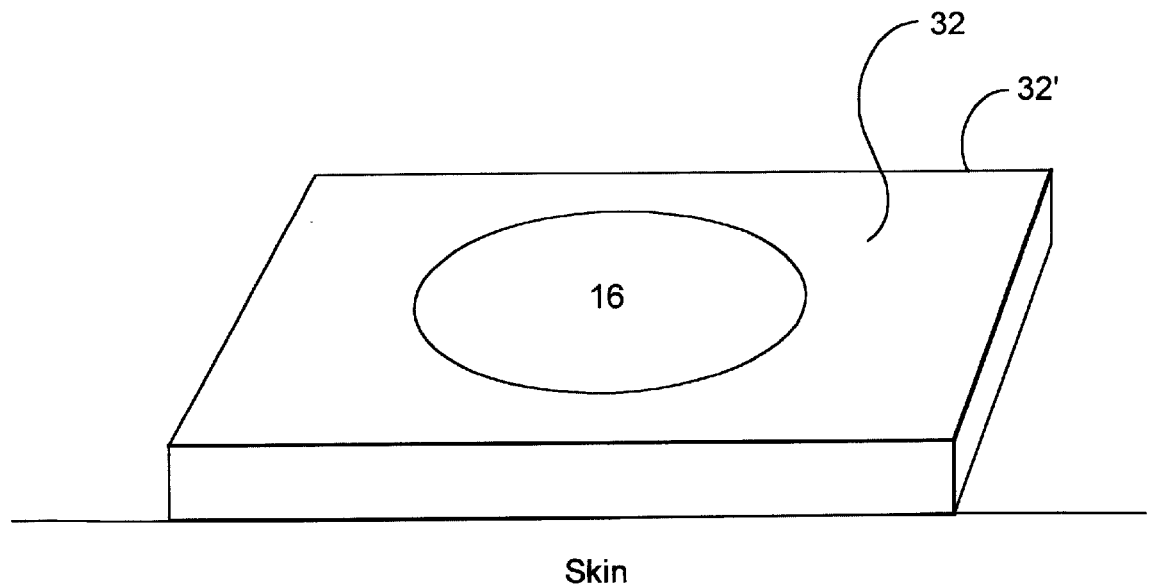
FIG. 10b is a perspective view of an embodiment of an electrode illustrating the use of an attached and/or conformable dielectric layer to achieve a uniform current density.

Referring to FIGS. 10a and 10b, other embodiments of the invention for achieving a more uniform thermal effect, involve the use of a layer of dielectric material coupled to the electrode and positioned between the conductive portions of the electrode and the skin. In one embodiment shown in FIG. 10a, all or a portion of electrode 16 can be coated with a dielectric material 32 to form a dielectric layer 32'. In a related embodiment shown in FIG. 10b, electrode 16 is attached to a dielectric layer or film 32', which can be made of a conformable material that conforms to the surface of the skin. In various embodiments, the electrode 16 that is attached to dielectric layer 32' can be of any geometry, e.g. circular, oval, rectangular, etc. It is desirable to have the surface of the dielectric layer 32' extend beyond the edges of electrode 16 such that substantially all current must flow through the dielectric layer. This can be achieved by configuring electrode 16 to have a smaller surface area than layer 32' and having electrode 16 substantially centered on the surface of layer 32'. Accordingly, electrode 16 can have between 1 to 100% the surface area of layer 32', with specific embodiments 25, 50, 75%, and 90%.

There are several key benefits to the use of dielectric layer 32' with electrode 16, the most important of which is the ability to produce a more uniform current flow through the electrode and subsequently to the underlying skin and tissue. This is attributable in part to a capacitance effect created by the use of layer/coating 32'. Specifically, the use of layer 32' creates an electronic capacitor (e.g., two conductors separated by an insulator) where, one conductor is the electrode, the second conductor is the skin or the tissue being treated, and the insulator separating them is the dielectric layer on the electrode. In various embodiments, the capacitive effect of dielectric layer 32 can be controlled through the selection of the thickness, surface area and dielectric constant of layer 32, as well as by controlling the frequency of the RF signal.

As a result of the above configuration, the dielectric coating creates an increased impedance to the flow of electrical current through the electrode. Owing to this increased impedance, and to the fact that electrical current naturally seeks the path of least impedance, the current is biased/forced to take the shortest path length between the two conductors, which is the path straight down through the electrode to the tissue. By corollary, the electrical current is unlikely to take any paths that would result in a longer path length and hence increased impedance. Such a longer path length would be the case for any concentration of current flowing out of the edges of the electrode.

The use of the dielectric coating serves to force a more uniform distribution of electrical current paths across the electrode surface and down into the tissue. This occurs because the capacitance resulting from the dielectric coating presents impedance to the flow of electrical energy particularly at the edges of the electrode, where current concentrations are likely to occur. More specifically, the use of dielectric coating 32' produces a more uniform impedance through the electrode and causes a more uniform current to flow through the electrode. The resulting effect minimizes or even eliminates, edge effects around the edges 16''' of electrode 16 which includes the perimeter for a circular disk-shaped electrode, and the perimeter and corners for a rectangular electrode. It is desirable to have the electrical impedance of the dielectric layer 32' to be higher than that of the tissue. In various embodiments, the impedance of layer 32' at the operating frequency, can be in the range of 200 Ω per square centimeter or greater. Suitable materials for a dielectric coating 32' include, but are not limited to, Teflon® and the like, silicon nitride, polysilanes, polysilazanes, polyimides, Kapton and other polymers, antenna dielectrics and other dielectric materials well known in the art.

Another advantage of using a dielectric layer 32' is that there is little or no increase in current density resulting from only partial contact of electrode 16 with the tissue surface. Normally, such partial contact would increase current density in the electrode portions remaining in contact with tissue increasing the size and severity of hot spots and the likelihood of spark discharge and burns to the tissue. However, because of the capacitance effect of the dielectric layer, the impedance of the electrode goes up (due to a decrease in the capacitance) as the surface area of the electrode tissue contact zone is reduced. This causes the current density flowing through the electrode to remain relatively constant. This effect is achieved by configuring the dielectric layer/electrode to have an impedance higher than the contacting tissue.

Hence, use of the dielectric coating on the electrode presents an important safety advantage over the use of just a conductive electrode in contact with the tissue, since there is little or no increase in current density and resulting hot spots from only partial tissue contact of the electrode.

Such partial contact with a conventional electrode, not only cause the edge effects and hot spots, but as the amount of tissue contact decreases, the current density can increase to the point where the electrode begins to act like a electrosurgical knife (e.g. a bovie) with a spark discharge causing serious burns to the patient and also possibly to the medical practitioner. In contrast for the dielectric-coated electrode, partial tissue contact at a point would result in almost no current flowing because the impedance would be very high. Thus, embodiments using the dielectric- coated electrode have safety advantages in the clinical setting where partial tissue contact often occurs.

Another advantage of the use of a dielectric coating is the minimization of the need to use a conductive fluid (e.g. saline solution) to conduct RF energy to the skin surface and/or assure electrical contact of the electrode with the skin surface. The use of conductive fluids minimizes tissue contact problems when the electrode is a conductive electrode. However for embodiments using a dielectric coating electrode, the conductive fluid is less important because the dielectric coating causes capacitively coupling of the energy into the tissue. This is a distinct advantage from several standpoints. First is from an ease of use standpoint, since fluids and/or conductive gels can be difficult to work with. The second advantage is one of safety and control, since the physician can not always control where the fluid goes, possibly heating and burnring tissue not intended to be treated, as well as presenting a possible shock hazard to the patient and medical personnel. The third advantage is reproducibility, since conductive fluids having different electrolyte concentrations will have different conductivities and hence, cause more or less current to be conducted to the tissue causing varying amounts of heating.

Figure 11:
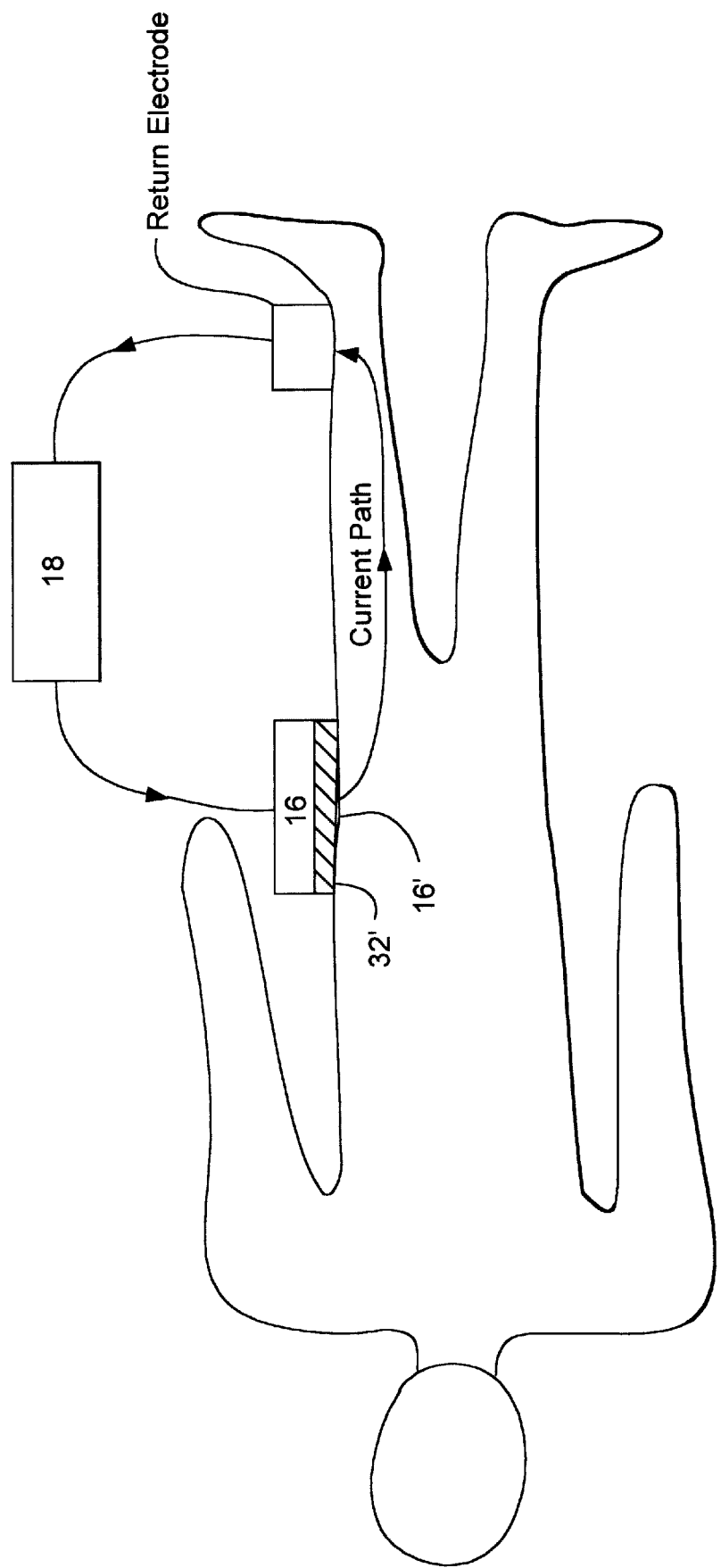
FIG. 11 is a schematic view illustrating the current path from the dielectric-coated electrode to the body and return electrode for monopolar electrode embodiments.
Figure 12:
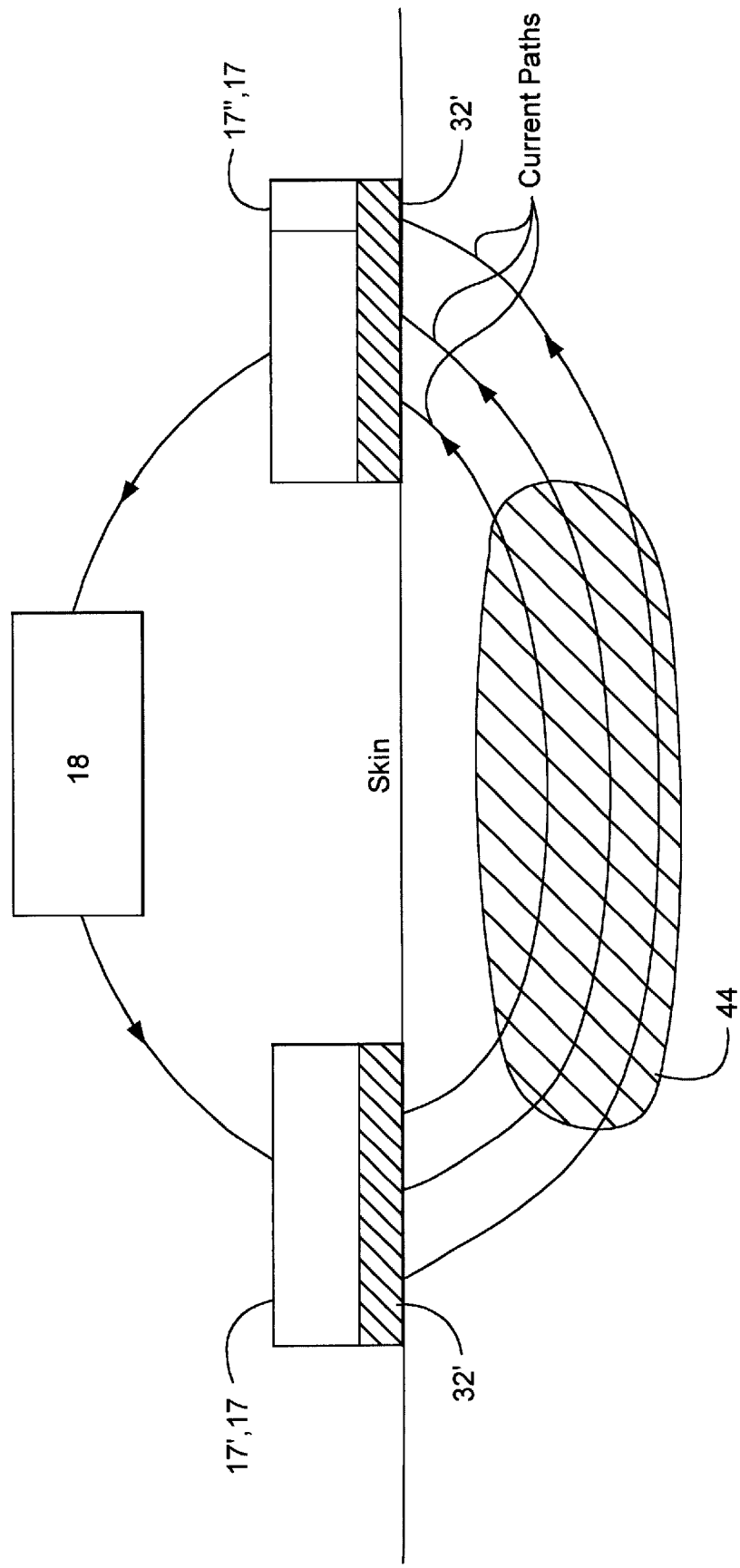
FIG. 12 is a schematic view illustrating the current through tissue for dielectric -coated bipolar electrode embodiments.

In various embodiments, a dielectric-coated electrode can be bi-polar or mono-polar. For a mono-polar configuration (shown in FIG. 11), electrode 16 can comprise a single electrode covered with a dielectric coating 32' that capacitively couples energy into the skin or other tissue used in conjunction with a return electrode 34. While for bi-polar embodiments, a capacitively coupled electrode can comprise multiple electrodes delivering energy to the skin. Referring now to FIG. 12, in one bi-polar embodiment (with the dielectric coating on the tissue contacting side), electrical current uniformly flows out from a first electrode 17' of a bi-polar pair 17 through its dielectric coating into the tissue then through the dielectric coating of the second electrode 17'' of the bi-polar pair 17 into the second electrode and then back to the RF energy source 18. The area of substantial current flow and hence the treatment zone 44 is substantially confined to an area of tissue between each bipolar pair 17 of electrodes. Because of the benefits of dielectric coating described herein, the current flowing through this area is very uniform resulting in a uniform thermal effect as well.

Figure 13:
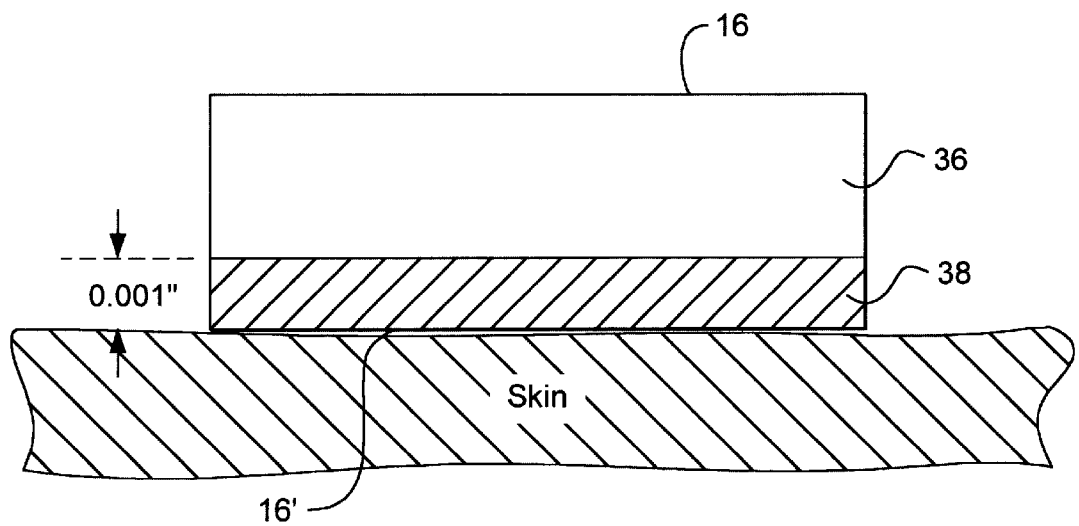
FIG. 13 is a lateral view of an embodiment of a dielectric-coated electrode where the dielectric coating comprises a copper coating on a polyamide substrate.

Referring now to FIG. 13, another embodiment of a dielectric coated/capacitively coupled electrode can comprise a copper coating 36 adhered to a polyimide substrate 38 that is about 0.001" in thickness. Such an electrode is similar to a standard flex circuit board material commercially available in the electronics industry; however in this case the flex circuit substrate (e.g. the polyamide layer) is much thinner than that found in a standard electric circuit board. The copper-polyimide laminate material can be an off-the-shelf commercially available material and the deposition of copper down on polyimide is a well-known process in the circuit board industry. However, the present invention uses this material in a fashion contrary to its standard or known usage or configuration. Specifically rather than having the copper in contact with the intended electrical device/circuit (e.g. the skin) as a conductive electrode, the polyimide is touching the skin and the copper is separated from the skin with the 0.001" (1 mil) polyimide layer. At standard electrosurgical operating electrical frequencies (e.g. several hundred KHz to perhaps a MHz), the 1 mil layer of polyimide is too thick and does not perform well as a capacitor from an electrical standpoint. One way of improving the performance of a 1 mil polyimide copper electrode is to increase the frequency of the RF current going to the copper-polyimide electrode. In various embodiments using 1 mill polyimide-copper electrodes, the RF current supplied to the electrode can be operated at approximately six MHz. In embodiments with a thinner polyimide layer (e.g. less than 0.001), the frequency of the RF current can be reduced to the standard range recited above. One method for decreasing the thickness of the polyimide layer would be to grow the copper layer on the polyimide using sputtering, electrodeposition, chemical vapor deposition, plasma deposition and other deposition techniques known in the art. These methods could be equally applicable to other thin polymer dielectric films known in the art. Alternatively these same processes could be used to deposit a dielectric layer such as paralyne, onto a conductive layer. Also, the copper layer could be adhered to a thinner 0.0003" polyimide film.

Figure 14:
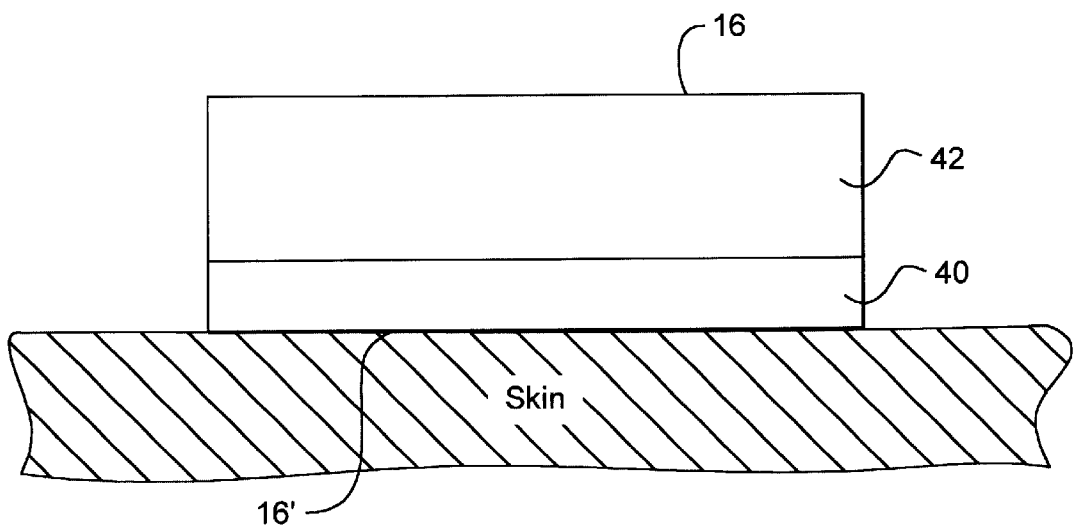
FIG. 14 is a lateral view of an embodiment of a dielectric-coated electrode where the dielectric coating comprises an oxide coating grown on a conductive substrate.

Referring now to FIG. 14, yet another embodiment of a dielectric-coated electrode involves growing an oxide layer (usually a metal oxide layer) 40, on a conductive material 42 such as a metal conductor. The use of oxide layer 40 presents a number of possible technical advantages. The first of which is a reduced thermal resistance and hence improved heat transfer through electrode 16 and ultimately through the skin verses metal-polymer film and other electrodes. specifically the thermal conductivity of a deposited oxide film (such as an aluminum oxide on an aluminum conductive layer) is significantly improved over that of a polyimide layer. This improves thermal conductivity, in turn improving the ability to cool and protect the skin by improving the transfer of heat from skin through the electrode, enabling the electrode to better dissipate heat from the skin (by convection and conduction) both with and without cooling of the electrode conduction. The net effect is to improve the cooling efficiency of the skin. For example, an aluminum oxide layer grown on an aluminum conductor has a thermal conductivity approximately 20 to 100 times better than a polyimide layer. Aluminum oxide layers can be readily grown on an aluminum using the commercially available process of anodization. The result is an electrode that has a dielectric layer 32', the aluminum oxide, which is also a very good thermoconductor. Oxide layers can also be grown on titanium, platinum, stainless steel, silver, gold and other conductors using similar anodization or other commercially available processes known in the art.

Thus, the use of dielectric-coated electrodes or otherwise capacitively coupled electrodes has one or more of the following advantages: i) improved the ability to uniformly treat tissue (e.g. more uniform thermal effect), ii) improved safety features such as partial tissue contact not resulting in burns, and minimizes the requirement for an electrically conducting fluid or electrolytic fluid to couple the electrode into the tissue; and iii) improved cooling ability for oxide coated electrodes such as an aluminum oxide coated aluminum electrode.

Figure 15:
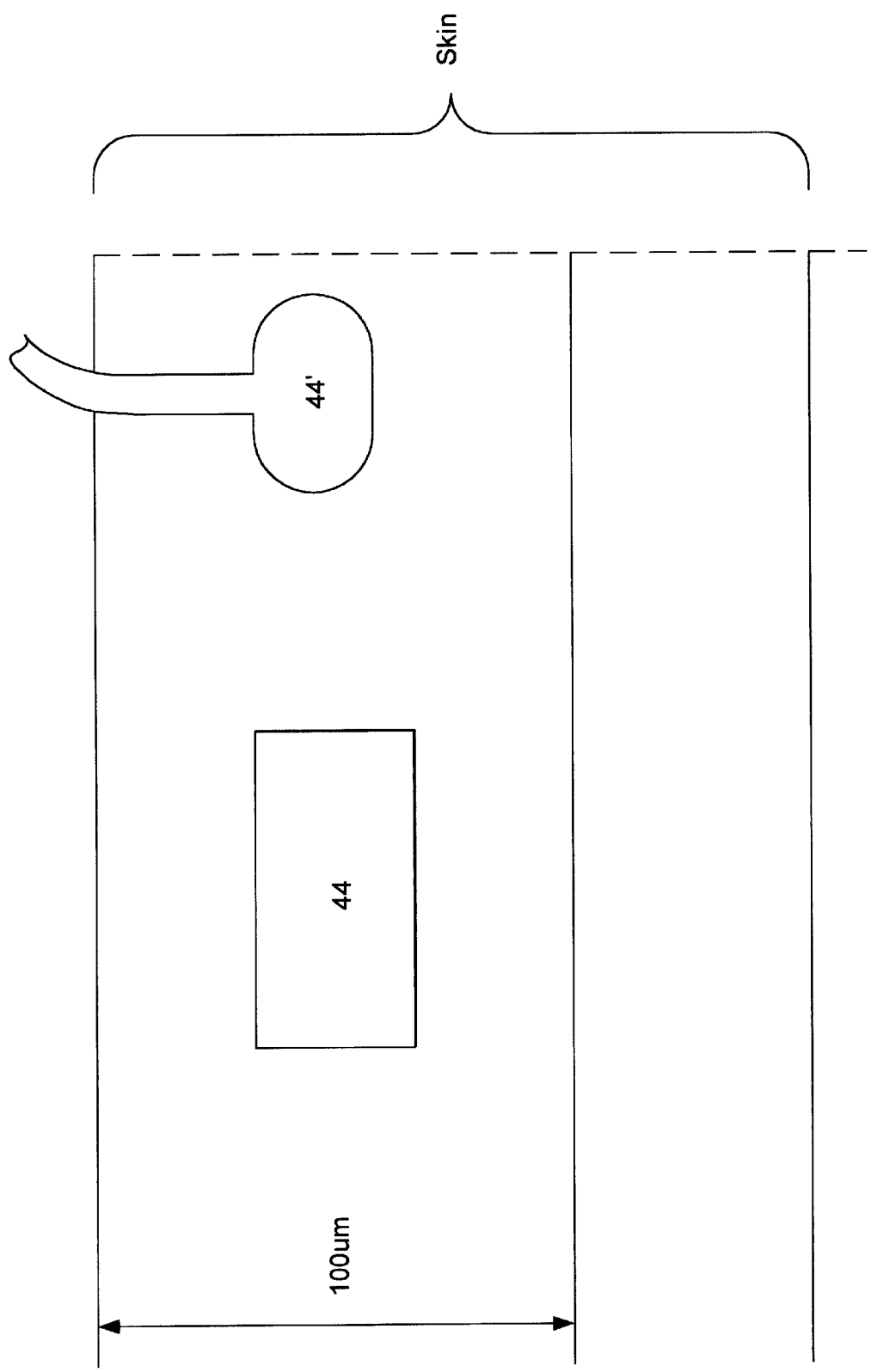
FIG. 15 is a cross-sectional view of the skin illustrating the target tissue zone and target tissue structures that can be treated by embodiments of the invention.

Referring now to FIG. 15, the target tissue zone 44 for therapy (also called therapeutic zone 44, or thermal effect zone 44), can include, but is not limited to, tissue at a depth from approximately 100 $\mu$m beneath the surface of the skin down to as deep as a couple of millimeters, depending upon the type of treatment (e.g. collagen contraction, hair removal, etc.). For treatments involving collagen contraction, it is desirable to cool both the epidermis and the superficial layers of the dermis of the skin which lies beneath the epidermis, to a cooled depth range between 100 m to several hundred m.

In various embodiments, the invention can be used to treat different structures 44' of the skin lying at different depths. Such structures can include the hair follicles and sebaceous glands and related structures. The invention can even be used to treat deeper structures or tissue such as the subcutaneous fat layer. Treatment in this case meaning the delivery of thermal or other energy to that tissue to produce a therapeutic effect. As such cooling may be important in each of these applications.

Figure 16:
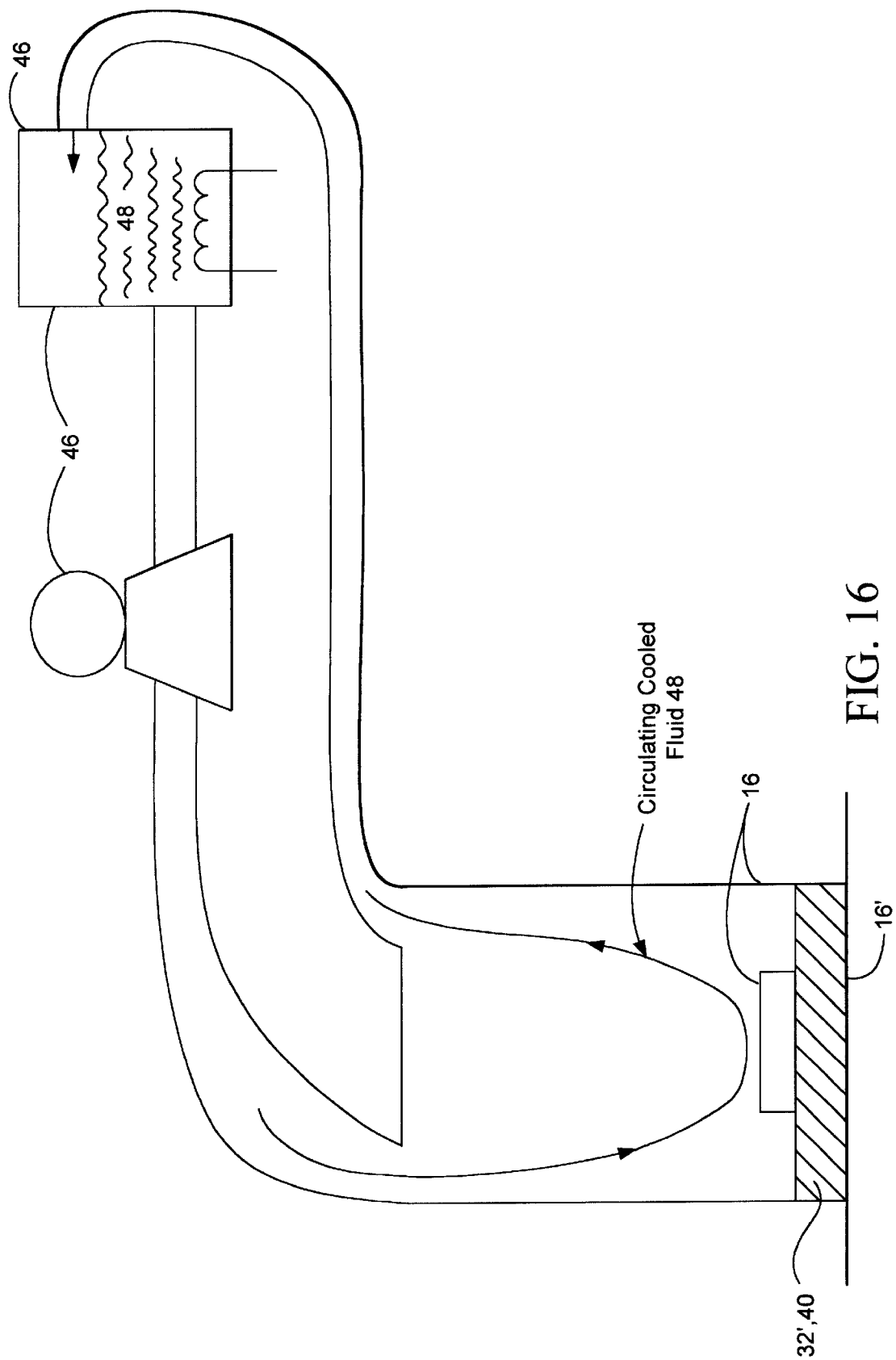
FIG. 16 is a cross sectional/schematic view illustrating an embodiment using a circulating cooled fluid to cool the electrode.

Turning now to a discussion of optimal control of the cooling process, all the devices disclosed in this application can incorporate some form of a cooling device 46, system 46' and/or method (see FIGS. 16 and 17). Cooling device 46 or system 46' can be configured to precool the surface layers of the target tissue such that when the electrode structure is in contact with the tissue and/or prior to turning on the RF energy source the superficial layers of the target tissue are already cooled. When RF energy source is turned on or delivery of RF to the tissue otherwise begins, resulting in heating of the tissues, the tissue that's been cooled is protected from thermal effects including thermal damage. The tissue that has not been cooled will warm up to therapeutic temperatures resulting in the desired therapeutic effect.

In various embodiments, the treatment process can include one or more of the following steps: i) precooling (before the delivery of energy to the tissue has started), ii) an on phase or energy delivery phase in conjunction with cooling, and iii) post cooling after the delivery of energy to tissue has stopped. Pre-cooling gives time for the thermal effects of cooling to propagate down into the tissue. More specifically, precooling allows the achievement of a desired tissue depth thermal profile, with a minimum desired temperature being achieved at a selectable depth. This can be facilitated with the use of thermal sensors positioned within or on the skin. The amount or duration of precooling can be used to select the depth of the protected zone of untreated tissue. Longer durations of precooling produce a deeper protected zone and hence a deeper level in tissue for the start of the treatment zone. The opposite is true for shorter periods of precooling, all other factors (e.g. RF power level) being relatively equal.

Post cooling can be important because it prevents and/or reduces heat delivered to the deeper layers from propagating upward (via conduction) and warming up the more superficial layers possibly to therapeutic temperature range even though external energy delivery to the tissue has ceased. In order to prevent this and related thermal phenomena, it is desirable to maintain cooling of the treatment surface for some period of time after application of the RF energy has ceased. In various embodiments varying amounts of post cooling can be combined with "real time cooling" and/or precooling.

Various embodiments of the invention may employ different cooling methods and those cooling methods can be configured for the specific treatment method or structure being treated (e.g. treatment of the sebaceous glands). Referring now to FIG. 16, one embodiment of cooling involves the circulation of a coolant or cold fluid 48, inside a hollow dielectric-coated electrode or other electrode structure such that this cooling fluid is an intimate contact with the electrode. As a result, when the electrode is in contact or close proximity to the skin, this cooling fluid also cools the skin via thermal conduction and/or radiation of heat from the skin to the electrode and then the transfer of heat from the electrode to the cooling solution by convection and conduction. In these and related embodiments it is beneficial to have good heat transfer through the cooling fluid, the electrode and the tissue to be cooled. Optimization of heat transfer through the electrode can be facilitated by the selection of materials (e.g. materials with high thermal conductivity such as metals), dimensions (e.g. thickness, etc.) and shape. Accordingly, heat transfer through the copper-polyamide electrode and related electrode embodiments can be optimized by minimizing the thickness of the polyamide layer. This will allow these types of electrodes to have good thermal coupling to the tissue. For the case of the metal oxide- metal electrodes (such as the aluminum-aluminum oxide electrode), metal oxide dielectric layer 40 has a much higher thermoconductivity than the polyamide dialectic, allowing a thicker dielectric layer and a thicker electrode. These factors allow for stronger electrode structure and potentially a higher degree of electrode capacitance and capacitive coupling.

Figure 17A:
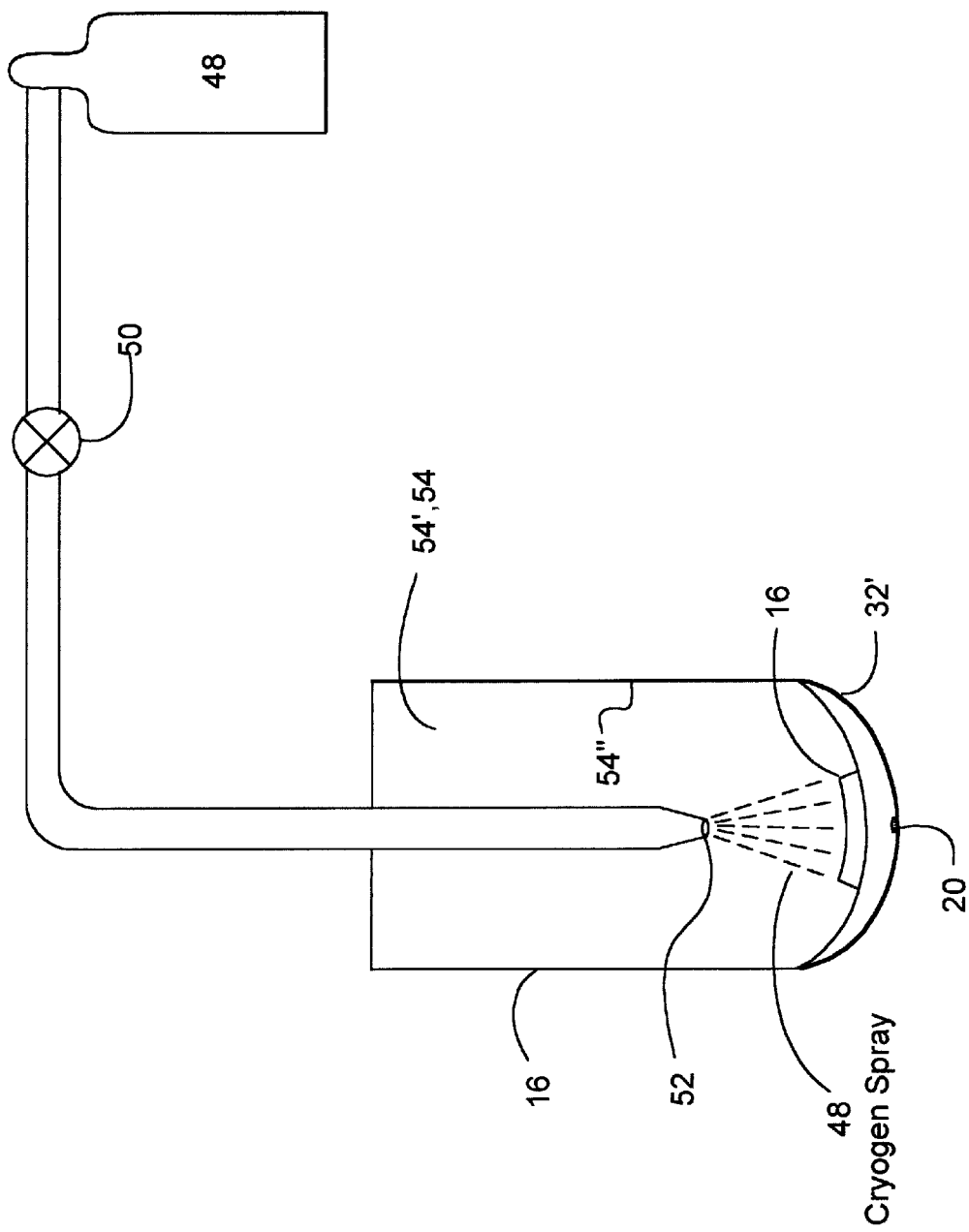
FIG. 17a is a cross-sectional/schematic view illustrating an embodiment using a coolant/refrigerant spray to cool an electrode within an electrode housing.

Referring now to FIG. 17*a,* other embodiments of the invention utilizing cooling can incorporate a spray valve 50 (or valve 50) coupled to a nozzle 52 positioned inside in the 54'0 interior of a hollow electrode structure/housing 54 of electrode 16. Nozzle 52 is used to spray a coolant or refrigerant 48 onto the inner surface 54" of the electrode structure 54, where it evaporates and cools the electrode. Refrigerant 48 cools the electrode 16 by combination of one or more of evaporative cooling, convection and conduction. The electrode in turn, cools the tissue that is beneath it through conduction. Possible refrigerants 48 include, but are not limited to, halogenated hydrocarbons, carbon dioxide and others known in the art. In a specific embodiment, the refrigerant is R134A which is available from Refron, Inc. (38-18 33rd St. Long Island City, N.Y. 11101) and commonly used to cool electronic components.

There are several advantages to cooling using an evaporating refrigerant (also known as a cryogen). First, this type of cooling known as evaporative cooling allows more precise temporal control of the cooling process. This is because cooling only occurs when the refrigerant is sprayed and it is evaporating (the latter being a very fast short lived event). Thus cooling ceases rapidly after the spray of refrigerant is stopped. The overall effect is to confer very precise time on-off control of the spray. Improved temporal control can also be obtained through the use of thin electrodes having negligible thermal mass, alone or in conjunction with a refrigerant spray. The negligible thermal mass of such electrodes results in an almost instantaneous cooling of the electrode and underlying skin.

Figure 17B:
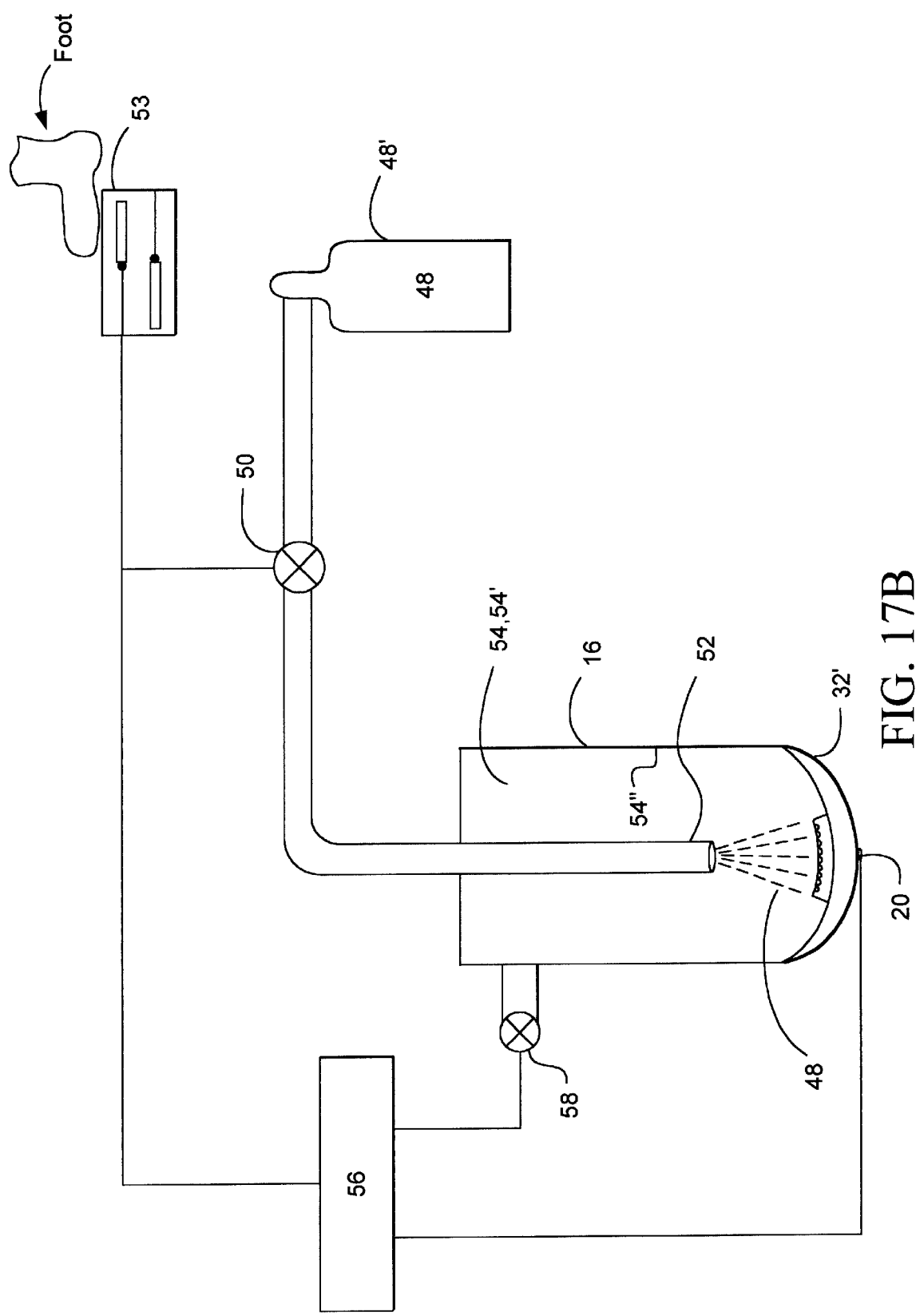
FIG. 17b is a related embodiment to that shown in FIG. 17a where the coolant spray is regulated by a solenoid valve coupled to an electronic control system and/or a physician-activated foot switch.

In another embodiment shown in FIG. 17*b,* spray valve 50 can be a solenoid valve 50, which can be fluidically coupled to a cryogen reservoir 48'. Solenoid valve 50 can be electronically coupled to and controlled by an electronic/computer control system 56 or manually controlled by the physician by means of a foot switch 53 or similar device. Such valves have response times on the order of five to ten milliseconds. Suitable solenoid valves include, but are not limited to a solenoid pinch valve manufactured by the N-Research Corporation (West Caldwell, N.J.).

In various embodiments, the electrode can have a variety of hollow structures which are simultaneously configured for spray cooling of the electrode and conductive cooling of the skin in contact with the electrode. This can be accomplished by a combination of one or more of the following i) maximizing the internal hollow surface area of the electrode, minimizing the wall thickness of the electrode in contact with the skin, and iii) designing the hollow area of the electrode to maximize the internal surface area that can be reached by the spray jet of a nozzle. It is also desirable to have an opening in the electrode, or chamber containing the electrode, to allow the evaporated refrigerant to escape. This escape can include a pressure relief valve to control pressure in the chamber.

In other embodiments involving use of refrigerants, cryogen 48 can be dispersed or sprayed through a porous or open cell structure (which can include the electrode) that can be configured to have cryogen 48 make direct contact with the skin if necessary. In another embodiment, the refrigerant is sprayed on the inside of a hollow electrode tubular structure, with the electrode external surface in contact with the skin. It is beneficial in this design to make the electrode surface strong enough (e.g. able to withstand compressive forces greater than 0.1 to 1 lbs) so that the electrode can support itself when pressed against the skin in order to improve heat transfer between the skin and the electrode. This can be accomplished through the selection of higher strength electrode materials, electrode thickness and shape. One embodiment of a structurally strong electrode involves the use of a metal oxide electrode such as titanium oxide electrode.

In alternative embodiments, portions of electrode 16 can be configured to be sufficiently flexible to conform to the skin, but still have sufficient strength and/or structure to provide good thermal coupling when pressed against the skin surface. Such a configuration can be utilized with a polyamide (or other polymer) copper film electrode that needs to be kept thin to optimize thermal conductivity. In these and related embodiments, the electrode may comprise or be integral to a hollow tissue probe that has a tissue contacting electrode external surface and an internal electrode surface that is integral to or otherwise exposed within an internal chamber of the probe where evaporation of the refrigerant takes place. The internal chamber of the hollow electrode 54 or probe is sealed, but can include a venting means 58.

In one embodiment shown in FIG. 17*b,* venting means 58 can be a pressure relief valve 58 vented to the atmosphere or a vent line. When the refrigerant spray comes into contact with the electrode and evaporates, the resulting gas pressurizes the inside of this sealed chamber/cylinder causing the thin flexible tissue contacting electrode surface to partially inflate and bow out from the surface of the supporting structure of the tissue probe. This inflated/pressurized configuration provides the thinner polyamide-copper film electrodes with a tissue contacting surface/structure with sufficient strength to provide good thermal coupling when pressed against the skin, while when in a deflated state or if there is no pressure in the chamber, the electrode remains flexible. In these and related embodiments, the refrigerant spray serves two purposes. First, to cool the electrode and the tissue adjacent the electrode, and second, to inflate/expand at least portions of the electrode and/or chamber carrying the electrode in order to provide an electrode/chamber structure configured for good thermal coupling to the skin. In various embodiments, the inflated electrode configuration can be configured to enhance thermal contact with the skin and also result in some degree of conformance of the electrode surface with the skin.

In various embodiments, relief valve 58 can be configured to open at pressures including but not limited to 0.1 psi to 30 psi, with a preferred narrower range of 0.5 to 5 psi and specific embodiments of and 0.5, 1, 2, 4, 8, 14.7, 20 and 25 psi. Also in various embodiments, the probe chamber can be fabricated from stainless steel and other machinable metals known in the art. Suitable pressure relief valves 58 include, but are not limited to, mechanical valves including spring actuated valves, polymer valves, and electronically controlled valves. In one embodiment pressure relief valve 58 can be of a mechanical type manufactured by the McMaster-Carr Corporation. The spring-actuated valves arc controlled by an internal spring opens the valve, when the pressure reaches a certain level. Embodiments using the electrically operated valves, can include a pressure sensor/transducer 20 positioned inside the chamber and an electronic controller 56 which is electronically coupled to both the electronic valve and the pressure sensor. The controller sends a signal to open the valve when a programmed pressure has been reached.

In various embodiments, cryogen spray 48 is used as cooling source through evaporative cooling and contact with the electrode that's touching the skin, and also to inflate a probe/electrode chamber to provide pressure which will inflate and/or bow out the thin flexible electrode to provide improved contact (e.g. thermal and mechanical) with the skin and also some degree of conformance with the skin. In embodiments employing higher chamber pressures, approximately 10 to 20 psi, the flexible thin polyamide electrode tissue contacting structure can become very rigid, and can have similar properties (e.g. stiffness, rigidity etc.) to Mylar®. Then, decreasing the pressure several psi (e.g. 1 to 4 psi) the rigidity decreases and the tissue contacting surface of the electrode begins to become conformable. Thus, the rigidity and/or conformity of the electrode can be selectable with chamber pressure and adjusted for the mechanical properties and shape of the skin surface being treated in order to obtain the desired level of thermal coupling to the skin. Chamber pressures between five to ten psi have been found to perform well for many applications. More rigid structures can be obtained at higher chamber pressures, and contrarily very flexible conformable structures can be obtained at lower pressures. In alternative embodiments, the use of a sealed evaporation chamber and "bowable" electrode could also be employed with electrodes having a dielectric oxide layer, such as the aluminum-aluminum oxide. In such embodiments, electrode thickness, surface length and support structure are configured to allow the electrode surface to bow outward with pressure in the 1 to 10 psi or other range disclosed herein. The flexibility of a metal electrode can be increased using one or more of the following approaches: by making the electrode thinner, increasing the unsupported length of the electrode surface and using materials/processing methods with reduced stiffness (e.g. Young's Modulus). In one embodiment an aluminum-aluminum oxide electrode could be in the form of a foil type electrode and may have a comparable thicknesses to commercially available aluminum foil.

Improved thermal response time is another advantage of embodiments using sprayed cryogen 48 for cooling purposes. Circulating water cooling systems have the limitation of not being able to have fast enough thermal response times due to a number of factors (e.g. thermodynamic properties of water, heat and mass transfer limitations, etc.). The use of the spray cryogens in combination with a thin film electrode (e.g. polyamide-copper) overcomes these limitations and provide& the capability to perform a number Of different types of algorithms for skin treatment that could not be performed with a circulating cold water cooling system. For example, the refrigerant spray could be turned on the order of milliseconds before the start of RF energy delivery to the desired tissue and subsequently cycled off and on in millisecond durations. In various embodiments this could be accomplished using commercially available solenoid valves coupled to a cryogen supply (e.g. a compressed gag canister) or the cryogen delivery loop. Such valves have response times on the order of five to ten milliseconds. In various embodiments, these valves could be coupled to a computer control system or could be manually controlled by the physician by means of a foot switch or similar device. One of the key advantages of this and related systems is the ability to rapidly respond and cool overheated tissue before the occurrence of thermal injury.

In alternative embodiment; the cryogen nozzle and solenoid valve can be coupled to or otherwise configured to be used with a chopper wheel (not shown). The chopper wheel is adapted for intermittently allowing the spray of the cryogen onto the tissue or electrode. This configuration provides the ability to shorten both the response time and the duration of cooling. In these and related embodiments, the cryogen spray is directed at an approximate perpendicular angle into the face of a chopper wheel that rotates at selectable angular velocity. The chopper wheel has an approximately circular geometry and has an open section, which can be a sector, radially oriented rectangle, or other geometric shape positioned at a selectable position on the face of the wheel. When the open section is aligned with refrigerant spray stream coming out of the solenoid valve then the spray goes down and hits the tissue. In various embodiments, the chopper wheel can rotate at angular velocities between 1 and 10,000 rpm. The wheel, wheel mechanism and timing system can be similar to those used on optical chopper wheels well known in the art. Alternatively, various high speed small motor mechanisms (such as a brushless dc motor) can also be used.

An important advantage of embodiments of the invention employing a solenoid valve alone, or in combination with a chopper wheel is the ability to deliver the cryogen in very short bursts (via spray or other means). This short burst capability allows the physician to titrate and/or selectively control the amount of heat removed by the cryogen from the tissue. This is because from a thermodynamic standpoint, the amount of heat removed by a given volume of a given cryogen as it evaporates is predictable (e.g. known latent heat of vaporization, known cryogen temperature, etc.) So for a milliliter volume of cryogen spray, the number of calories of heat loss from the tissue can be predicted with a reasonable degree of accuracy (e.g.. approx +/−5% or better). This information can be used to design a treatment algorithm that's very quantitative, e.g. the amount of cooling delivered is correlated to the RF power level or other metric of energy delivery. Moreover, the algorithm can be configured to control the amount of thermal energy (e.g. heating) delivered to the tissue in an accurate manner in order to obtain a desired tissue temperature and/or effect at selectable depth and similarly can control the amount of cryogen delivered to the tissue to produce a selectable amount of cooling sufficient to protect non target tissue from thermal injury. Such ratios of cooling delivered to energy delivered can be preprogrammed into the algorithm and can be configured for depth of tissue to be treated, type of tissue (e.g. skin vs. adipose tissue), thermal conductivity of treated skin or tissue, desired target tissue temperature and desired maximum non target tissue temperature. For example, when delivering RF power at a 100 watt level for 0.1 second (assuming that 50% of this heat propagates upward to a non target skin/tissue site), the volume of cryogen delivered would have to be able to cool/remove 5 joules of energy from the tissue. If each ml of cryogen spray removed one joule of energy by evaporation, then 5 ml of cryogen would have to be delivered to the tissue. This could be delivered in the same 0.1 seconds as the energy delivery or could be delivered in series of ten 0.010 second burst over 0.2 seconds with 0.2 ml of cryogen per spray burst.

A key advantage of the cryogen spray is the availability to implement rapid on and off control, with the 0.005 second response times for solenoid valves, or even faster with embodiments using some type of electronically controlled aperture or shutter known in the art. In various embodiments, a varied number of pulse on-off type cooling sequences and algorithms may be employed. In one embodiment, the treatment algorithm comprises precooling the tissue by starting a cryogen spray, followed by a short pulse of RF energy into the tissue, with the cryogen spray continuing during the duration of the energy delivery and then stopping shortly thereafter (e.g. on the order of milliseconds). This or another treatment sequence could be repeated again. Thus in various embodiments, the treatment sequence can comprise a pulsed sequence of cooling on, heat, cooling off, cooling on, heat, cool off, and with cooling and heating durations on orders of tens of milliseconds. In these embodiments, every time the surface of the tissue of the skin is cooled, heat is removed from the skin surface. However this cooling effect is not appreciable for the deeper tissue away from the surface area where the cryogen spray is directed and having its effect. In various embodiments, the cryogen burst duration and interval between burst can be in the tens of milliseconds ranges which allows surface cooling, while still delivering the desire thermal effect into the deeper target tissue.

In various embodiments, the burst duration and interval can be adjusted for the heat transfer rate/thermoconductivity between deeper target tissue and the skin such that the cooling rate of the skin equal or exceeds the rate of heat transfer from the RF heated deeper target tissue to the skin. The rapid response time and precise temporal control of embodiments of the invention employing burst cryogen spray cooling allows the performance of a number of noninvasive tissue treatment methods that could not be performed by apparatus/methods employing water and other slower, less controllable cooling methods due to a risk of thermal injury of nontarget tissue and other thermal related complications. Such noninvasive treatment methods include skin resurfacing, collagen shrinkage, treatment of sebaceous glands, hair follicle removal, treatment/removal of subcutaneous fat and other skin treatments known in the art of dermatology or plastic surgery.

In various embodiments, the depth of the thermally effected zone (also called the thermal effect zone) can be controlled by the amount of precooling. Specifically, the longer periods of precooling (for a given rate of energy delivery, or total amount of energy delivered), result in a deeper penetration in the tissue before the thermal effect starts. In contrast, little or no precooling results in the thermal effect starting at or near the skin surface. In related embodiments, the thickness of the thermal effect zone in the tissue can be controlled by the duration of the RF energy delivery. The longer the period of RF energy delivery, the deeper the thermal effect.

In still other related embodiments, the starting depth and thickness of the thermal effect zone can be selected through control of both the duration/amount of precooling and the duration of RF energy delivery. Such control presents a distinct advantage in that it allows the selected treatment of a discrete anatomical layer or tissue structure located at various depths within or beneath the skin without injury to surrounding tissue. This and other benefits can be derived from the combination of cryogen spray with pulsed cooling and/or heating.

Figure 18:
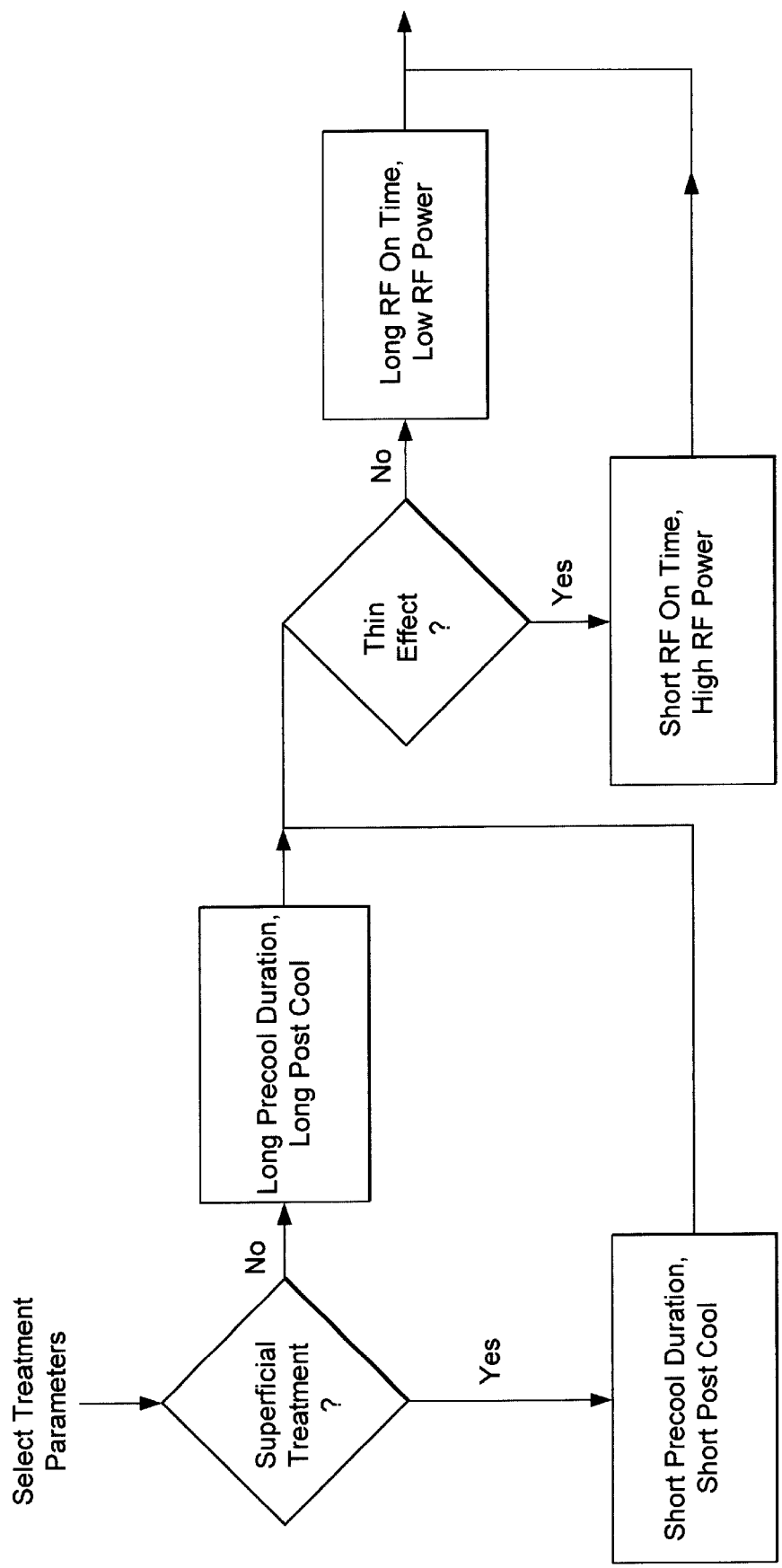
FIG. 18 is a flow chart for the selection of treatment parameters such as cooling and heating sequences, durations etc.

Different treatment algorithms can incorporate different amounts of precooling, heating and post cooling phases in order to produce a desired tissue effect at a desired depth. FIG. 18 is a flow chart for the selection of treatment parameters including, duration of precooling, RF on time, RF power levels, and postcool durations for treatment algorithms for different tissue depths discussed herein, including superficial, thin effect and deep tissue treatments.

Figure 19:
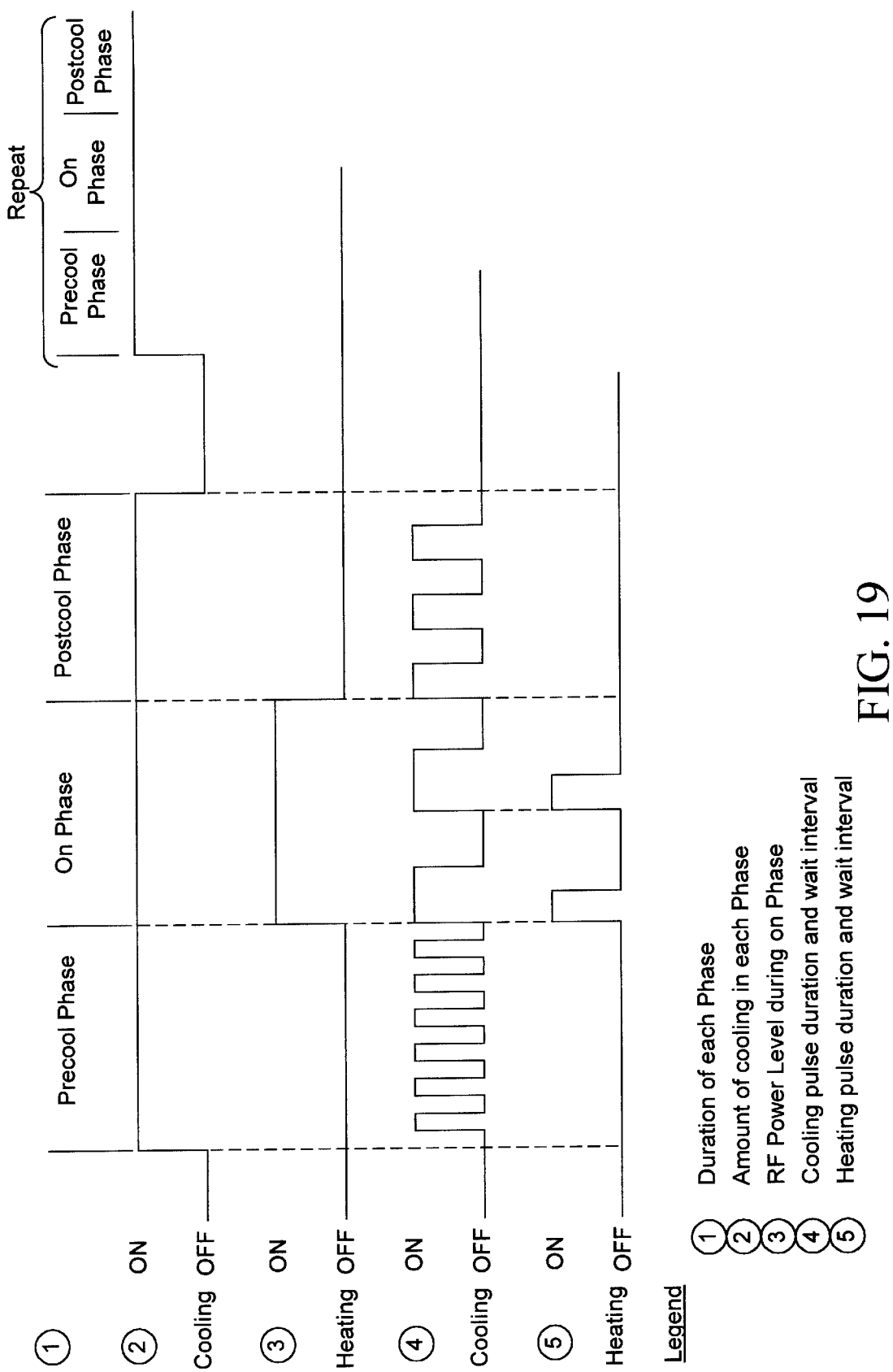
FIG. 19 illustrates various embodiments of duty cycles cooling and heating during different phases of treatment.

FIG. 19 shows various duty cycles (e.g. on times) of cooling and heating during the different phases of treatment. The figure illustrates the specific duty cycles (e.g. on-times and interval between on-times) of cooling and heating during the stages of pre-cooling, energy delivery (heating) and post cooling. The cooling and heating duty cycles can be controlled and dynamically varied by an electronic control system known in the art. Specifically the control system can be used to control the electronic solenoid valve (described herein) for controlling the flow of coolant and the RF generator supplying RF energy.

In various embodiments, the invention can include sensors to measure parameters such as the skin surface temperature, the interior or exterior temperature of the electrode structure, the dielectric layer temperature, or the tissue temperature at a selectable depth. Accordingly, sensors 20 can be positioned in the interior or exterior of the electrode structure and adjacent dielectric layer 32'. One or more sensors 20 can be coupled to electronic control system 56 and can be used to control the delivery of one or both energy and cooling to the skin and target tissue, Suitable temperature sensors and sensor technologies include thermocouples, thermistor, infared sensors/technology and ultrasound sensors/technology. The latter two being well suited for measuring temperature at tissue sites located down inside the tissue as opposed to near or on the surface. Such sensors enable the measurement and generation of temperature depth or thermoprofile of the tissue. Such a thermoprofile could be used for process control purposes to assure that the proper amounts of heating and cooling were being delivered to achieve a desired elevated deep tissue temperature while maintaining skin tissue layers below a threshold temperature for thermal injury. The physician would use the measured temperature profile to assure that they were staying within the bound of an ideal/average profile for a given type of treatment (e.g. sebaceous gland treatment).

In addition to the treatment methods discussed herein, in other embodiments the invention can be configured for skin rejuvenation. In these embodiments, the delivery of thermal energy to the target tissue is controlled/reduce to only cause a wound healing response and not necessarily collagen contraction. This would healing response results by delivering thermal energy to the tissue to induce a condition called fibroplasia. This is a condition in which there is a proliferation or otherwise infiltration into the dermis of a large number of fibroblast cells. These fibroblast cells in turn, lay down or deposit collagen into or adjacent the thermal affect zone causing the skin rejuvenation process. However by delivering a selected amount of energy, a proportion of the fibroblasts in the dermis can be killed off. As a result, a wound healing response occurs, in which there is large infiltration of fibroblasts into the dermis, with a large number of fibroblasts present than before treatment. These new fibroblasts lay down new collagen as part of a wound healing response and this rejuvenates the skin. Thus by controlling the amount of thermal energy delivery to the target tissue (and/or temperature of), the resulting tissue affect can be titrated to produce skin rejuvenation for lower levels of delivered energy, or collagen contraction configured to tighten the skin for higher levels of delivered energy. If the collagen contraction/skin tightening is positioned very superficially, it can help to minimize the appearance of wrinkles. If the area of collagen contraction is located deeper in the dermis, it can tighten up areas of loose skin.

As discussed herein, various embodiments of the invention can employ either mono-polar or bi-polar electrode implementations. One bi-polar embodiment shown in FIG. 20 can comprise very dense arrays of small electrodes 16 where every other electrode in the array is an opposite pole of a bi-polar electrode pair. The electrode array in this embodiment will produce a very superficial delivery of thermal energy into the tissue extending from one bi-polar pair to another. In contrast, a mono-polar electrode will produce a much deeper tissue affect than will the bi-polar electrodes. This depth difference in thermal affect between the two types of electrodes results from the difference in current paths for mono-polar versus bi-polar electrodes. For mono-polar electrode configurations, the current flows from the positive electrode to a return electrode located far away on the patient's body. In contrast for a bi-polar electrode pair, all the current paths are localized between electrode pairs located on the electrode array (e.g the energy delivery device).

In various embodiments, different electrode configurations can be employed for different targeted tissue layers or sites or for different forms of treatment to the same site. For example, when treating deeper target tissue layers (e.g. >100 $\mu$m tissue depth) such as the subcutaneous fat or the deep dermis, a mono-polar electrode configuration could be selected for its ability to delivery energy to the deeper tissue sites. In other embodiments treating more superficial tissue layers (e.g. 100 $\mu$m tissue depth), for example wrinkle removal, a bi-polar electrode configuration would be preferable. In various bi-polar electrode embodiments, the depth of the thermal tissue affect is limited to the more superficial tissue layers with little or no deep tissue effect, even for longer periods of energy delivery. Accordingly, various bi-polar embodiments can be readily configured for use with continuous cooling system/apparatus either in the form of a continuous spray or a circulating fluid. The use of continuous cooling presents several advantages in that i) more conventional and potentially less expensive cooling systems (e.g. water cooling, air cooling and the like) can be employed, ii) the complexity of the system or apparatus is reduced in that reduced hardware and soft resources are required to control the delivery of coolant; and iii) improved ease of use for the medical practitioner.

Many current dermatological procedures involving the delivery of heat to tissue are done with lasers. However, the use of lasers for dermatologic procedures has several technical drawbacks which limit the access and depth of tissue treatment, reduce efficacy and cause undesirable patient complications. First, laser light propagating in tissue exhibits a phenomena known as scattering in which the incident light is scattered by incident cells and tissue from its original optical path. This scattering results in the incident light beam no longer traveling in a straight, and hence, predictable path within the target tissue. The scattering has the further detrimental effect of causing nonuniform intensity within the beam surface and hence a nonuniform thermal effect in the tissue contacted by the beam. Specifically, the outer areas of the laser beam undergo more scattering than the interior or more central portions of the beam. This causes the central portions of the beam to become more focused as the beam propagates deeper into the tissue or in other words, the central portion becomes more intense while the outer areas and beam edges less intense. This nonuniform beam intensity can in turn lead to non-uniform heating and tissue effects as the beam moves deeper into the tissue and becomes increasingly focused on a smaller and smaller area. This non-uniform intensity can readily cause a nonuniform cosmetic effect. More importantly it may be significant enough to cause severe thermal injury with related medical complications (e.g. burning, damage or destruction of nerves, blood vessels, etc.).

Various mono-polar electrode embodiments of the present invention provide improvements and features for overcoming these and other limitations. They also provide the medical practitioner with an apparatus generally better suited for treating the skin and underlying tissue including the deeper dermal and subdermnal tissue. These improvements/advantages include a more uniform delivery of energy in the target tissue beneath the surface of the electrode and dispersement of delivered energy outside the target tissue site. This is attributed to i) the more uniform current density of dielectric coated mono-polar electrodes and ii) the tendency of current density (and hence energy density) in mono-polar electrodes to diffuse (as opposed to becoming concentrated) as it spreads out and travels through the body to the return electrode, becoming negligible outside the tissue treatment site. This actually has some advantages over other methods of heating the tissue.

Figure 20:
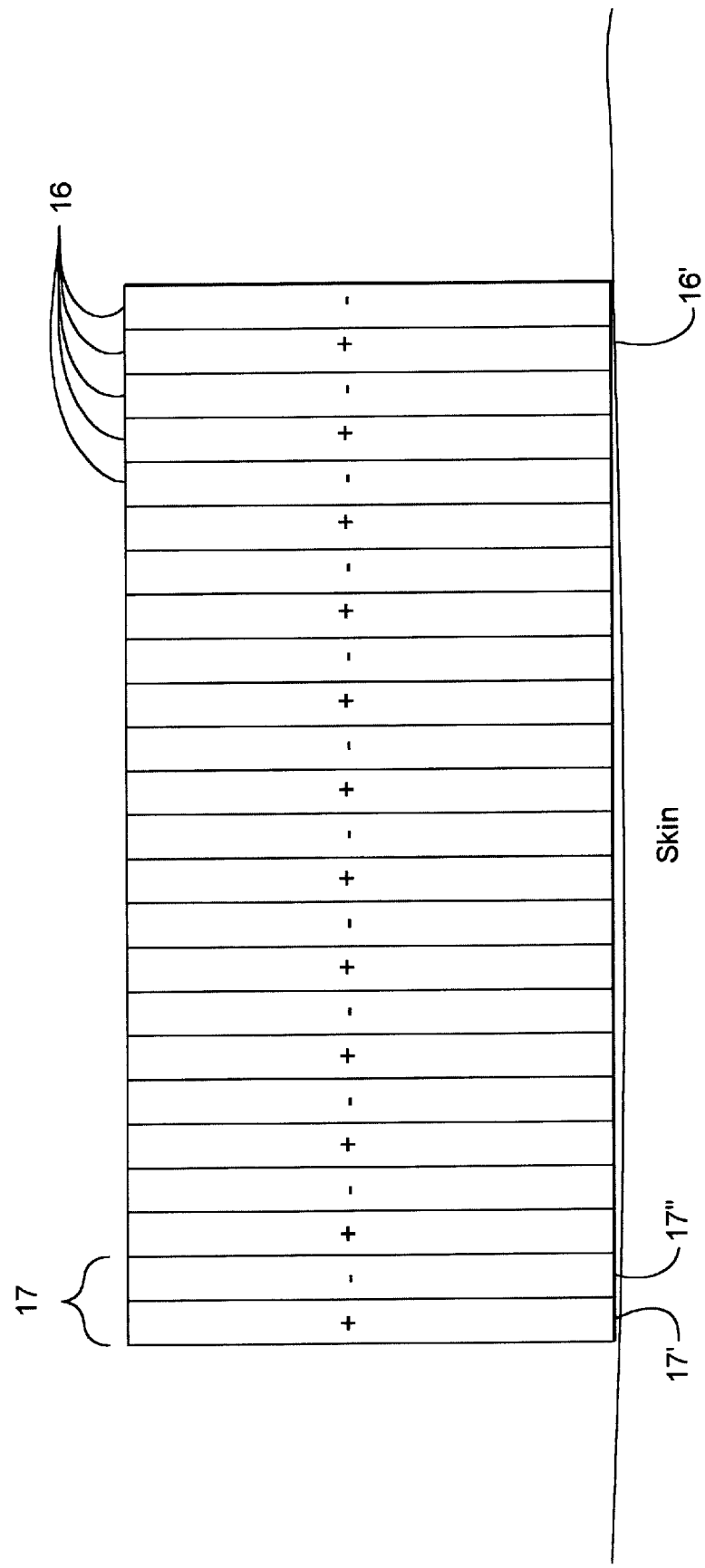
FIG. 20 is a cross-sectional view illustrating a bipolar electrode embodiment comprising a dense array of multiple electrodes.

In various embodiments the bi-polar electrodes can comprise an array of electrodes, including a highly dense array of electrodes. As shown in FIG. 20, such an array can include a multiple bar pattern of electrodes, where every other electrode of a sequence of thin rectangular bars is an electrode of a bi-polar pair. In embodiments where the electrodes are located very close to each other tissue, thermal effects (e.g. treatment) tends to occur in the tissue underlying gap between the electrodes. In various embodiments the gap between electrodes of a bi-polar pair can include but is not limited to a range from 0.0001 to 1 inch, with specific embodiments of 0.001, 0.010, 0.025, 0.050, 0.1, 0.25 and 0.5 inches. As the distance between electrodes comprising a pair increases, the electrodes begin to behave like mono-polar electrodes. That is they are not influenced by the presence of another electrode that may be in the same or other tissue treatment area. In various embodiments, the electrode spacing or electrode gap can be varied or modulated along one or more axis of an electrode array. In one embodiment with a linear array of rectangular electrode, the electrode gap can be controllably varied in the longitudinal direction in order to tailor the resulting pattern of thermal/ tissue affect in the targeted tissue. Portions of the linear array can have a very small electrode gap producing a near continuous affect, while other portions can have a wider gap producing discrete zones of thermal affect with adjacent substantially untreated zones. In various embodiments an intermediate electrode gap could be chosen to achieve both a bi-polar and mono-polar effect in terms of depth and pattern of the thermal effect. To avert any potential edge effects with bi-polar electrodes, dielectric coating and capacitive coupling could be used on bi-polar pairs as well as mono-polar pairs.

Another drawback of the use of lasers in dermatologic procedures such as skin resurfacing is the fact that the procedure has to be done in patchwork fashion. Specifically a small area of the face is treated, approximately one square centimeter area, either with a laser that has a beam that's that size, or a beam that has a smaller beam diameter and some kind of a scanning mirror system that would result in the beam moving over a one square centimeter area. The nature of this procedure is a discrete or patchwork delivery of energy/treatment to one small area at a. So one square centimeter is treated and the laser is moved to next area. Consequently, it is a very time consuming and arduous process. Also it can result in the necessity of coming back for treatment sessions in separate visits to the physician with the patient having to undergo the undesirable side affect (e.g.. redness, blistering, etc.) each time.

Using various embodiments of the invention discussed herein, a similar discrete treatment method could employed. However the use of cooling would prevent/reduce the occurrence of blistering and burning. Specifically the apparatus may be used to treat one square centimeter skin, using the spray cryogen to achieve a pre, inter or post cooling affect as needed. After treating the fist area of skin the electrode/device would be lifted off the surface the skin and moved to the next area (e.g. square centimeter) of skin to be treated with this procedure being repeated until the entire desired target skin/tissue site was treated.

In alternative embodiments the procedure could be done in a quasi-continuous or even a continuous fashion. One embodiment of treatment method would involve a quasi-continuous pulsed method where a short spray of pre-cooling is done, then a short application of RF energy, followed by a short spray of post-cooling and then a period of waiting where the physician observes the physical appearance of the skin as well as monitoring the skin and/or tissue temperature using sensor described herein. The procedure is then repeated as needed until the entire desired target site is treated.

In a related embodiment, the procedure could be done in an even more continuous fashion with a painting or sliding motion of the energy delivery device/electrode across the surface of the skin. In these embodiments both cooling and heating application sequences would be done in a more continuous fashion and the pulsing method (e.g of cooling and heating) is one approach that lends itself to that. In these embodiments, cycles of cooling, heating and cooling could be done between five and ten times a second, or even faster. The depth of the tissue effect could be increased with a longer RF heating phase (which could be pulse or continuous) and if necessary a longer period of precooling. The use of bi-polar electrode configurations would be particularly well suited for continuous treatment embodiments using continuous cooling and heating, since the depth of current flow, and hence energy delivery, for bi-polar configurations is limited. The ability to treat tissue in more continuous fashions where the device/electrode is slid across the surface of the skin is a distinct advantage over the use of laser treatment used to treat discrete areas of skin in a patchwork approach.

The continuous skin treatment methods (e.g. by sliding the electrode) afforded by embodiments of the present invention would be particularly advantageous/desirable to surgeons and other physicians who typically use their hands during medical procedures would rather have a instrument where they can have some control over movement of the instrument. Moreover the apparatus of the present invention presents the further advantage of allowing physicians to utilize their surgical skills and manual dexterity to achieve a finer and precise level of control over the delivery of the treatment and hence the quality of the clinical outcome versus laser devices that can only be used to treat skin in a noncontinuous patchwork fashion. The use of more continuous treatment with embodiments of the present invention could also significantly shorten procedure times. Also if the physician wanted to deliver more treatment in anyone spot he/she leaves the electrode/device there a little bit longer. This allows the physician to titrate the treatment effect in different areas of the target tissue.

Another advantage of various embodiments of energy delivery devices (e.g., dielectric-coated cryogen cooled electrodes) adapted to slide over the skin and deliver RF energy in a near continuous fashion is greater access to different areas of tissue where a laser could not get easily get access or would otherwise be obstructed. Such areas include parts of the body with pronounced curvature, acute angles or otherwise rough and uneven surfaces.

In various embodiments of the invention, collagen-containing tissue is treated by controllably delivering thermal and/or mechanical energy through the epidermis to the collagen containing tissue so as to change a physical feature or property of the epidermis through the thermal modification of the collagen containing tissue. In various embodiments, the physical feature can be one or more of the following, a reduction in size of a wrinkle in the epidermis, a reduction in an elastosis of the epidermis, an improvement of an epidermis contour irregularity, a tightening of the epidermis, remodeling of the underlying collagen containing tissue site, remodeling of the epidermis, changes in three-dimensional contouring, and combinations thereof.

The collagen containing tissue can be in a dermal layer, a deep dermal layer, a subcutaneous layer underlying a dermal layer, in fat tissue, and the like. Intracellular modification of the epidermis and skin appendages can also be achieved. A reverse thermal gradient, wherein the temperature of the epidermis is less than a temperature of the collagen containing tissue, can be used to create the composition of matter. With the reverse thermal gradient, the surface temperature of the skin can be at, above or below body temperature. When the composition of matter is created there is controlled cell necrosis of the epidermis, the collagen.

As used in the application "in vivo" refers to the thermal, mechanical and/or magnetic modification of tissue within a living composition of matter.

An aesthetic composition of modified living matter is a composite three dimensional phenotype that is comprised of a remodeled preexisting cutaneous container of preexisting soft tissue contents. The aesthetic composition of matter can include combined remodeling of the soft tissue contents and its container. Matrix interactions of collagen with energy involve native or preexisting collagen and/or the de novo production of nascent collagen by the induction of the wound healing sequence. These interactions are produced by the molecular and cellular remodeling of the collagen matrix. Molecular remodeling of the extracellular matrix occurs from the contraction and distraction of preexisting collagen fibrils. Cellular remodeling of the matrix is a delayed phenomenon and involves the activation of a wound healing sequence with fibroblast contraction and nascent collagen production as a static supporting structure of the remodeled matrix.

Electromagnetic and mechanical modalities are used to remodel the matrix and to alter intracellular metabolism. These modalities may be applied separately or in a coupled device geometry. Coupled mechanical force reduces the energy requirement to create a specific morphological result and is typically applied externally.

For many aesthetic applications, contact with the skin by the energy source is required. An alternating electrical current may be used to remodel the extracellular collagen matrix of the dermis and subcutaneous tissue. However, weaker magnetic fields can also be employed to delicately modify the intracellular metabolism of these structures including the epidermis and skin appendages. More rapid phenotypic changes can occur from electrical remodeling of the extracellular matrix than magnetic modification of intracellular processes of the epidermis and skin appendages. Rather than producing observable changes, magnetic modification may also be used for maintenance or homeostasis of the aesthetic phenotype.

The visual perception of animate matter is due to a composite electromagnetic field of component atoms in various soft tissue structures. The human perception of animated matter is also determined and restricted by the limited span of the visual spectrum in comparison to the entire electromagnetic spectrum.

Methods of detecting the electromagnetic field (EMF) of animate matter by using a larger electromagnetic (EM) spectrum (than the visual spectrum) can provide a delineation of EMF patterns not typically seen by the human eye. Changes in this broader EM spectrum may be detected before they become visually apparent. The pattern of change in the EMF may be used as a diagnostic modality before phenotypic changes of aging occur in tissue. These previously non-visualized changes in the EMF of individuals may provide an early warning signal before these changes become morphologically apparent. Furthermore, manipulation of the EMF pattern to a more youthful EMF profile may provide the means to limit or reverse the morphological expression of this aging process.

Ablative methods include non invasive and minimally invasive removal of subcutaneous fat in addition to resurfacing of the skin. Non-ablative methodologies remodel skin and soft tissue with a minimum of cellular and extracellular necrosis. Both ablative and non-ablative methodologies are used to create an aesthetic composition of matter (ACM).

Depending upon the type of aesthetic composition of matter to be formed, a treatment modality matrix is created to determine the most effective combination of electromagnetic energy, mechanical force, method of application (ablative or non ablative) and tissue interaction (molecular vs. cellular remodeling). However, central to this matrix is the use of an energy source, including but not limited to electromagnetic energy, to alter the extracellular collagen matrix and intracellular metabolism of the epidermis and skin appendages with a minimum of collateral damage to tissues that do not require modification. Complimentary application of mechanical force can be used to lower electromagnetic energy requirements and potential side effects of treatment. The pattern of thermal energy delivery is no longer a random Brownian process. Instead, energy delivery becomes a directed process that produces a specific morphological effect without collateral tissue damage. Ablation is avoided entirely or it is created selectively to limit thermal side effects in creation of the composition of matter. As a result, an aesthetic composition of modified living matter is reliably created that is either an entire phenotype or a constituent component of a whole.

Vectors of external mechanical compression can be used to smooth surface wrinkling by conforming dermal defects within a preheated collagen matrix of the collagen containing tissue site. A partial phase transition of a matrix can be created at a lower temperature. As a result, the clinical effectiveness is enhanced while side effects of treatment are concomitantly reduced.

A more in-depth description of skin anatomy is required to understand the interaction of energy with its component parts. The epidermis is the cutaneous barrier to the outside world and is provided by the keratin bilipid layer of the stratum corneum which is produced by the continuing upward maturation of keratinocytes within the epidermis. Thermal and biological components of the skin barrier are created from this maturation process. The solar or ultraviolet component of the barrier is provided by melanocytes that reside in basilar layer of the epidermis. Melanin granules are produced in these cells which are then distributed to upwardly migrating keratinocytes by dendritic extensions of the cell membrane. An additional population of melanocytes and keratinocytes is also present in the skin appendages. These structures are the hair follicles, sebaceous and sweat glands which are present in the deeper dermal and subdermal levels. The dermis is the main structural support of the skin and is immediately subjacent to the epidermis. This supporting layer is mainly comprised of collagen fibrils that are subdivided into papillary and reticular component. The more superficial papillary dermis is immediately subjacent to the epidermis and is less dense than the deeper reticular dermis.

Burns are the morphological result of thermal energy interactions with skin and are classified into first, second and third degrees on the basis of dermal depth. A first-degree burn is a thermal injury that extends superficially into the epidermis and does not involve blistering or ablation of the skin. A temporary erythema of the skin occurs that resolves within twenty-four hours. A healing or reepithelialization process is not required. A second degree burn is a deeper thermal injury that extends into the dermis for a variable depth and is characterized by blistering and crusting. Ablation of the epidermis occurs with destruction of the dermis at either a superficial or deeper level. Superficial second-degree burns extend into the papillary dermis and are readily heal by reepithelialization because the skin appendages are not destroyed. For deeper second degree burns, a greater portion of the dermis is ablated which may complicate healing and reepithelialization. With a deep second degree burn, many of the skin appendages are destroyed in addition to the loss of normal dermal architecture.

Thinning and disruption of normal dermal anatomy can permanently alter the texture and elasticity of the skin. For many of these burn patients, a plastic or translucent appearance of their face is apparent. Obviously, a thinner margin of safety is present in deep second degree burns. For this reason, deeper second-degree burns are more frequently converted to burn scar deformities than more superficial burns. A third degree burn is characterized by the full thickness destruction or ablation of all skin layers including the skin appendages. Healing by reepithelialization does not occur normally but is achieved by the lengthy healing process of secondary intention. Unless surgically closed the burn wound can form granulation tissue that slowly contracts to close the open rent in the biological barrier. Excessive scarring and deformity is likely. A thin scar epithelium is typically formed over the burn scar. This fragile biological barrier is easily disrupted with minor trauma. Repeated ulceration of the burn scar may even require subsequent revisional surgery.

Aging of the skin can also be classified in a manner similar to thermal burns. Wrinkling is mainly caused by depletion of collagen matrix in the papillary dermis. This intradermal or second-degree deficit is a more superficial contour deformity than glabellar or nasolabial creases which are full thickness dermal defects that extend through the entire papillary and reticular dermis.

Resurfacing of the skin can also be classified in a manner similar to thermal burns. After ablation of the epidermis, skin appendages play a central role in the reepithelialization process. Skin appendages are present in different densities depending upon the specific area of the body. The highest density is present in the fascial skin where current laser modalities of resurfacing are practiced. Skin appendage density in other areas such as the neck, trunk and extremities is inadequate to provide a consistent pattern of reepithelialization. The skin appendages, consisting of hair follicles and sebaceous glands, contain keratinocytes and melanocyte that are the crucial components of reepithelialization. Diminution in either cell population has significant ramifications in the reestablishment of a functional epidermal barrier. With deeper second degree resurfacing, there is also an increased risk that treated areas can be more easily converted to a third-degree burn if the reepithelialization process is protracted or if this process is complicated with infection.

Following reepithelialization, a four to eight month period of burn wound maturation ensues that is characterized by hyperemia and transparency in which the skin appears shinny and pink. Thinning of the remodeled dermis produces a porcelain texture of the skin that is similar to the faces of many burn patients. Although wrinkling is diminished, this alteration of normal skin texture remains a permanent feature of a patient's face.

The use of a conformance-energy delivery device offers benefits of enhanced clinical outcomes and a reduction of treatment side effects. Enhanced clinical outcomes include a greater effectiveness to correct superficial and deep wrinkling of facial skin. Duration and pain during the healing period are significantly reduced as the level of resurfacing is more superficial. A conformance-energy delivery device can be safely applied to areas outside the face because the depth of dermal ablation has been minimized without loss of clinical effectiveness. Skin tightening of treatment areas is also provided while simultaneously correcting surface irregularities.

With an appropriately shaped energy delivery surface, the ability exists to shape the skin envelope into a desired three dimensional contour. These benefits are possible while minimizing surface ablation. Use of the conformance-energy delivery device reduces side effects by lowering the amount of thermal energy needed to resurface a treatment area. With this device, superficial resurfacing is capable of achieving deeper thermal effects. Healing from a superficial second degree resurfacing reduces the depigmentation and texture changes that are more common with deep second degree resurfacing. A prolonged period of erythema is avoided. Instead of an operating room, patients can be treated in an office setting without the occupational risks of a laser.

With the composition of modified living matter of the present invention, a matrix of different operational modes can be used to create different tissue effects. A "pressing" or stationary mode of application with convection cooling can conform the skin surface with minimal ablation. In this instance, wrinkles and creases are treated by selectively heating and conforming the dermis. Skin tightening without ablation is also performed in this particular mode of application.

A different mode of application is used to treat sun damaged skin or residual wrinkling that is not corrected by non-ablative applications. The device is applied in a mobile fashion similar to "ironing" a shirt. Mobile compression without convection cooling creates the present composition of matter resulting in a resurfacing of the skin and application of shearing vectors of force that additionally smooth the matrix.

A matrix of different modes of application can be created depending upon the clinical circumstances. For example, a cold iron (convection cooling with shearing and compression) may be ideal in conditions that require maximal smoothing of surface contour without ablation. This mode of application provides the greatest benefit in the hip and thigh areas where contour irregularities of cellulite are severe but solar damage is minimal. Patients with severe wrinkling of the face without solar damage may also benefit from this particular permutation.

The creation of the composition of modified living matter of the present invention can employ the creation of a reverse thermal gradient and involve other strategies to avoid the blistering of skin. Hydration facilitates the passage of an electrical current through the epidermis by reducing surface impedance. Another significant effect is the increase in thermal conductance of the stratum corneum. Tissue components such as the keratin/lipid bilayer of the stratum corneum are poor thermal conductors and function as thermal insulators to preserve the overall heat content of the patient. Hydrated stratum corneum is a better thermal conductor which promotes heat transfer to underlying collagen containing tissues. The collagen containing dermis that has not been hydrated can behave as a thermal insulator as well as an electrical resistor. As a result, the thermal content of the target collagen containing tissue is increased selectively.

Energy delivered to the soft tissue system, defined by the collagen containing tissue site, remodels the collagen matrix by disrupting the intermolecular crosslinks within the fibril. Although temperature is a measure of heat content, an accurate measure of energy delivery to the tissue is required. Measure of dose rate and overall dose to the tissue is required to determine the most effective control parameters. Dose rate is important due to the time dependence of thermal conduction, thermal convection and relaxation processes. Total dose is also important as there are a known number of molecules to be contracted with a required amount of energy per molecule. Another factor that affects the heat content of tissue is the thermal dissipation that occurs through thermal conduction away from the target tissue and the thermal convection from vascular and surface structures.

In contrast to the application of energy, manipulation of energy losses to the collagen containing tissue underlying the epidermis provides another means to avoid surface ablation. Thermal conduction losses occur through the passive dissipation of heat through tissue and is limited by local tissue parameters. In contrast, convective heat transfer occurs through the physical movement of heated matter away from the target tissue and is a process that can be actively manipulated. Sequential flash cycles of surface cooling and tissue heating provides a reverse thermal gradient as the heat dissipated from surface convection occurs faster than subdermal tissues. Cycles of surface cooling and tissue heating are performed with a thermal energy source. A progressive increase in the subdermal heat content occurs while maintaining a constant surface temperature. This occurs because the removal of heat by surface convection is more rapid than thermal conduction within the dermis. Other approaches to reduce the thermal load to the skin surface can be employed. Multiple port focusing with ultrasound in a tandem fashion can have a similar effect of dispersing energy. A combination of these modalities may be employed to avoid thermal damage to the epidermis.

Additionally, in creating the composition of the present invention, the stability of the collagen triple helix can be chemically altered prior to thermal denaturization. The collagen shrinkage temperature (Ts) is an indication of molecular stability and is determined by the amount of cross linkage. Reagents such as hyaluronidase (Wydase) that enzymatically decrease fiber stability can reduce the shrinkage temperature (Ts). Typically, a reduction of 10 C. in the Ts is obtained by the injection of this reagent. As a result, power requirements to target collagen containing tissues are reduced. The solution can be combined with a dilute local anesthetic and injected into target tissues with the "tumescent" technique.

Thermal shrinkage, or tightening of the underlying collagen containing tissue can be provided without the destruction of the overlying epidermis. This process of molecular contraction has an immediate biophysical effect upon the matrix and is based upon the cleavage cascade of intramolecular and intermolecular bonds within the collagen fibril. Skin tightening with thermal contraction and remodeling of collagen can correct areas such as the thighs, knees, arms, back and hips without unsightly scarring of standard techniques. Areas previously corrected by surgical procedures, such as face and neck lifts, could also be corrected without requiring surgery or the typical incisions around the ear. Elastosis, or stretching of the abdominal skin from pregnancy, can be corrected without the long scar commonly associated with an abdominoplasty. Thermal remodeling of underlying collagen containing tissues is effective, non-invasive alternative for the aesthetic treatment of these areas.

Treatment of "cellulite" of the thighs and hips is another example. Typically, the subcutaneous fat layers have loculations from fibrous septae that contain collagen. These fibrous septac call be remodeled to tighten the soft tissue in areas such as the hips and thighs. Additionally, dermal and subdermal telangiectasias (spider veins) are diminished by the contraction of the matrix adjacent to these vessels.

Another component of electromagnetic remodeling is cellular remodeling of collagen containing tissues with a thermal-conformance device. The use of low level thermal treatments over several days provides an additional way to contract skin without blistering. The cellular contraction process is initiated and involves the inflammatory/wound healing sequence that is perpetuated over several days with sequential and lengthy low level thermal treatments. This cellular contraction process is a biological threshold event that is initiated by the degranulation of the mast cell that releases histamine which initiates the inflammatory wound healing sequence. Histamine alters endothelial permeability and allows the creation of inflammatory edema. In this tissue system, contraction of skin is achieved through fibroblastic multiplication and contraction with the deposition of a static supporting matrix of nascent scar collagen. The nascent matrix is simultaneously remodeled with a conformance template that is incorporated in the thermal energy delivery device. For many aesthetic and functional applications, molecular and cellular effects occur in tandem with each other.

With the application of a conformance template, surface irregularities with depressions and elevations have vectors directed to the lowest point of the deformity. Prominent "pores" or acne scarring of the skin have a similar pattern to cellulite but on a smaller scale that can also be corrected. The application of pressure reduces the power required to remodel the matrix and should diminish surface ablation. Compression can also exert electrical impedance and thermal conductivity effects that can allow delineation within different components of collagen containing tissues.

Aesthetic conformers with a thermal energy source can also be used to remodel the subcutaneous fat of hips and thighs in addition to the tightening of the skin envelope. Digital capture of a preexisting aged contour is used to digitally form an aesthetic three dimensional contour that subsequently provides the means to fabricate a conformance template. Additional aesthetic applications include congenital prominence of the ear in which the convolutions (antehelical fold) are altered by remodeling the collagen within the cartilage. The nasal tip can be conformed to a more aesthetically pleasing contour without surgery.

A conforming aesthetic template can be used with any process that remodels underlying collagen containing tissue. In addition to the thermal remodeling of collagen, chemical modalities that invoke the wound healing sequence can be combined with a conforming esthetic template. Glycolic acid can induce a low level inflammatory reaction of the skin. Scar collagen and fibroblastic (cellular contraction) are directed by converging and diverging vectors created from a conformer that smooths and tightens the skin envelope into a more desirable contour. Additionally, a softer and more compliant skin texture in achieved.

Figure 21:
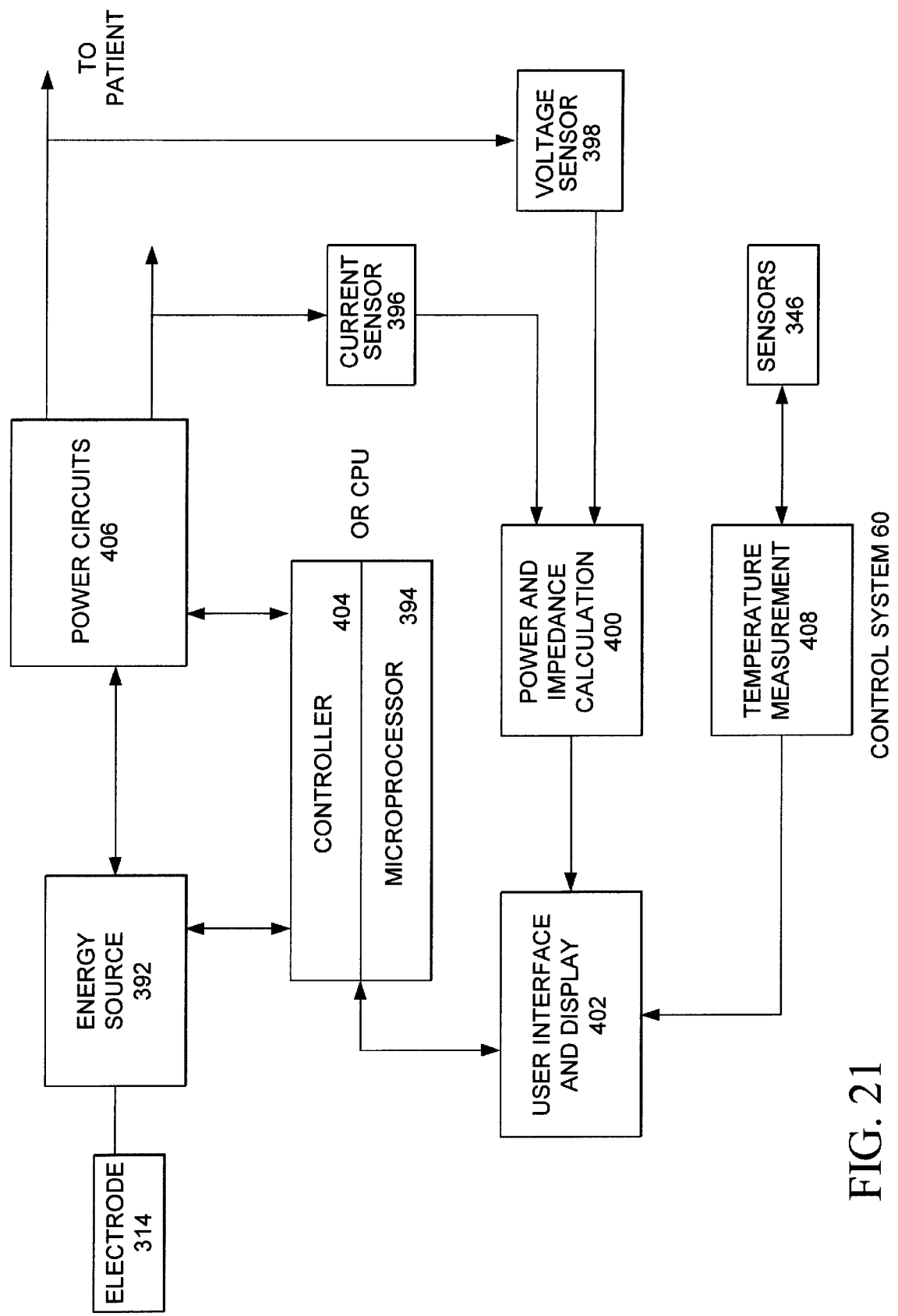
FIG. 21 depicts a block diagram of the feedback control system that can be used with the pelvic treatment apparatus.

Referring to FIG. 21, in an embodiment, skin treatment apparatus 10 can be coupled to an open or closed loop feedback system/resources 60. As shown in FIG. 21, feedback system 60 couples sensor 346 to power source 392. For purposes of illustration, energy delivery device 314 is one or more RF electrodes 314 and power source 392 is an RF generator, however all other energy delivery devices and power sources discussed herein are equally applicable.

The temperature of the tissue, or of RF electrode 314 is monitored, and the output power of energy source 392 adjusted accordingly. The physician can, if desired, override the closed or open loop system. A controller 394 or microprocessor 394 can be included and incorporated in the closed or open loop system 60 to switch power on and off, as well as modulate the power. The closed loop system utilizes microprocessor 394 to serve as a controller to monitor the temperature, adjust the RF power, analyze the result, refeed the result, and then modulate the power. More specifically, controller 394 governs the power levels, cycles, and duration that the radio frequency energy is distributed to the individual electrodes 314 to achieve and maintain power levels appropriate to achieve the desired treatment objectives and clinical endpoints. Controller 394 can also in tandem, govern the delivery of cooling fluid. Controller 394 can be integral to or otherwise coupled to power source 392 and can also be coupled to a fluid delivery apparatus. In one embodiment controller 394 is an Intel® Pentium® microprocessor, however it will be appreciated that any suitable microprocessor or general purpose digital or analog computer can be used to perform one or more of the functions of controller 394 stated herein.

With the use of sensor 346 and feedback control system 60 skin or other tissue adjacent to RF electrode 314 can be maintained at a desired temperature for a selected period of time without causing a shut down of the power circuit to electrode 314 due to the development of excessive electrical impedance at electrode 314 or adjacent tissue. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output in an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of energy when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output in an appropriate amount in order to maintain the desired temperature delivered at the sensor 346. A multiplexer can be included to measure current, voltage and temperature at sensor 346. Energy can be delivered to RF electrode 314 in monopolar or bipolar fashion.

Controller 404 can be an analog or digital controller, or a computer with driven by control software. When controller 404 is a computer it can include a CPU coupled through a system bus. On the system can be a keyboard, disk drive, or other non-volatile memory systems, a display, and other peripherals, as are well known in the art. Also coupled to the bus are a program memory and a data memory. Also, controller 404 can be coupled to imaging systems including, but not limited to, ultrasound, thermal and impedance monitors.

The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 22:
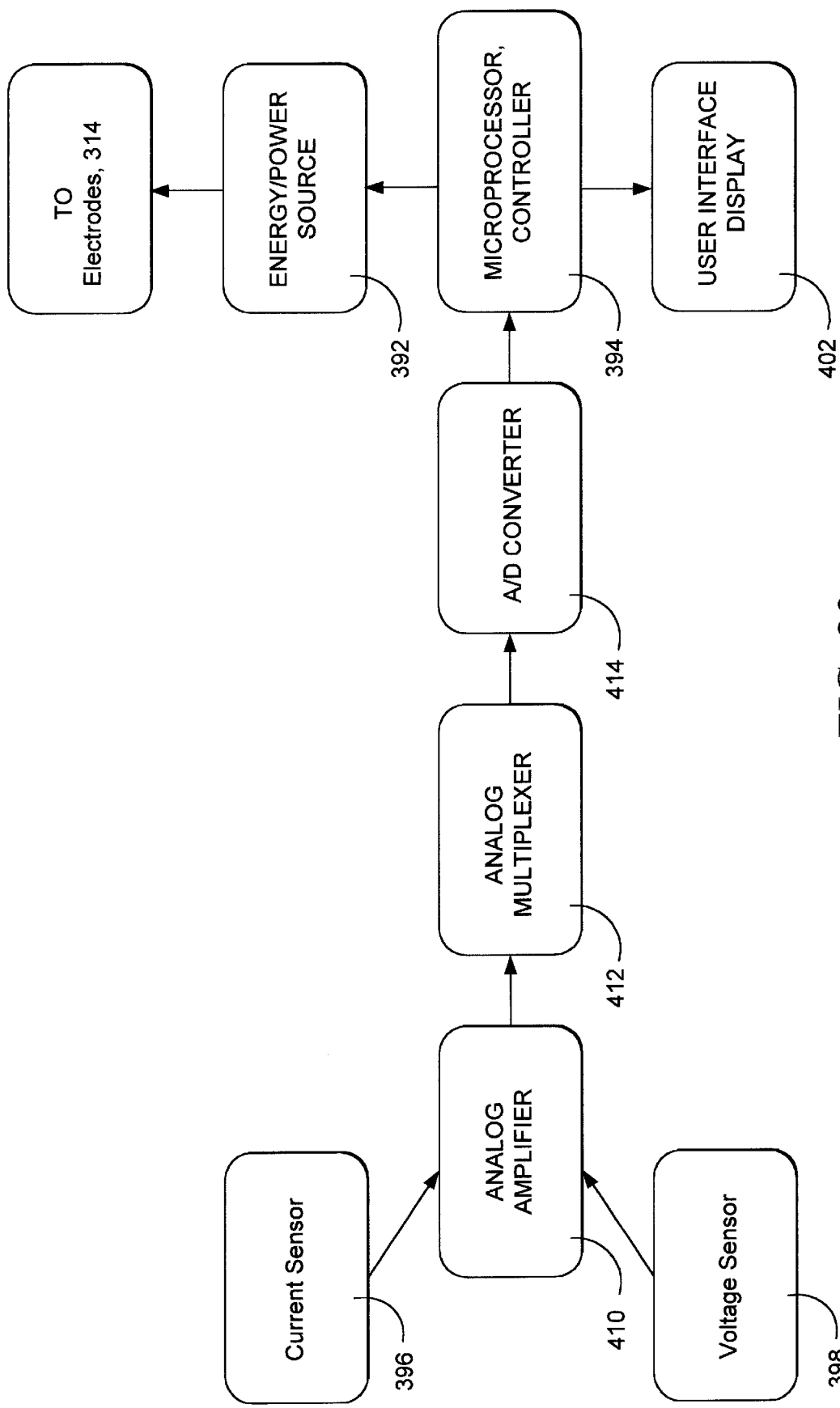
FIG. 22 depicts a block diagram of an analog amplifier, analog multiplexer and microprocessor used with the feedback control system of FIG. 21.

Referring now to FIG. 22, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394.

Microprocessor 394 sequentially receives and stores digital representations of impedance and temperature. Each digital value received by microprocessor 394 corresponds to different temperatures and impedances. Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 23:
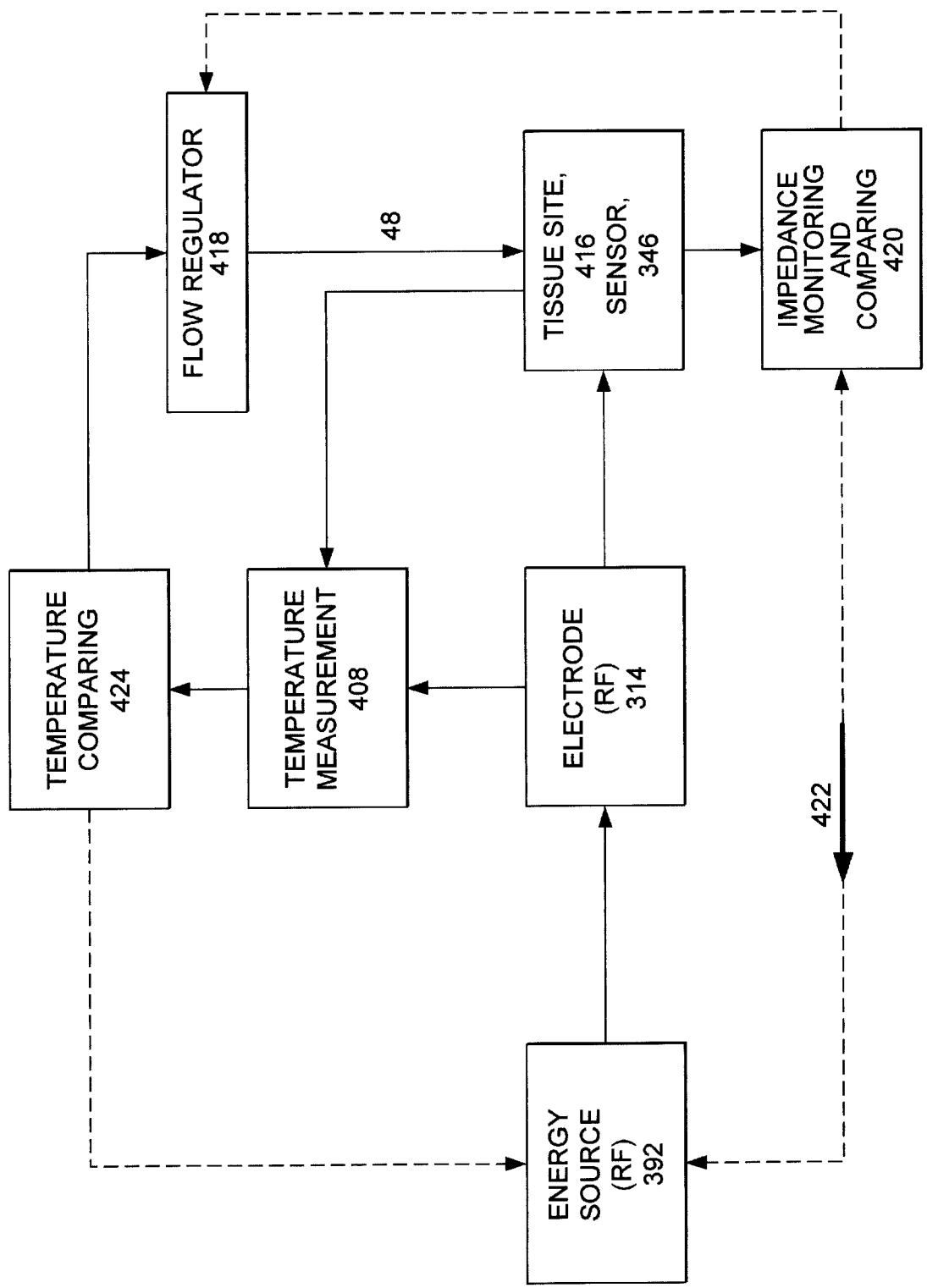
FIG. 23 depicts a block diagram of the operations performed in the feedback control system depicted in FIG. 22.

FIG. 23 illustrates a block diagram of a temperature and impedance feedback system that can be used to control the delivery of energy to tissue site 416 by energy source 392 and the delivery of cooling solution 48 to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If the measured impedance exceeds the set value, a disabling signal 422 is transmitted to energy source 392, ceasing further delivery of energy to RF electrode 314. If the measured impedance is within acceptable limits, energy continues to be applied to the tissue.

The control of the flow of cooling solution 48 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the tissue temperature is too high, comparator 424 sends a signal to a flow regulator 418 (which can be intergral to a pump 418) representing a need for an increased cooling solution flow rate. If the measured temperature has not exceeded the desired temperature, comparator 424 sends a signal to flow regulator 418 to maintain the cooling solution flow rate at its existing level.

The foregoing description of a preferred embodiment of the invention hag been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for treating a tissue, comprising:
   a handpiece assembly;
   a dielectric electrode coupled to the handpiece assembly and including at least one RE electrode with a front surface and a back surface that is physically and electrically coupled to a back surface of a dielectric, at least a portion of the dielectric configured to contact a tissue surface; a cooling media delivery member coupled to the dielectric electrode and configured to deliver a cooling media to the back surface of the RF electrode; and
   a sensor coupled to the dielectric electrode.

2. The apparatus of claim 1, wherein the dielectric electrode is configured to reduce at least one of an edge effect, an electrode edge effect, an electrode temperature gradient an electrode current density gradient or a tissue interface surface temperature gradient.

3. The apparatus of claim 1 wherein the sensor is a thermal sensor, a thermocouple, an optical sensor, a current sensor, voltage sensor, an impedance sensor or a flow sensor.

4. The apparatus of claim 1, further comprising:
   a source of cooling media coupled to the cooling media delively member.

5. The apparatus of claim 4, wherein the cooling media is one of a cooling fluid, a gas, a cryogenic gas, a liquid, an electrolytic solution, a cooled liquid or a cryogenic liquid.

6. The apparatus of claim 1, wherein the handpiece includes at least one of a connector, an electrical connector, a cooling media connector, a lumen, a fluid lumen, a cooling media lumen; a flow control device, a control valve or a nozzle.

7. The apparatus of claim 1, wherein the dielectric electrode includes a tissue interface surface.

8. The apparatus of claim 7, wherein the tissue interface surface has a shape configured to conform to an anatomical structure.

9. The apparatus of claim 8, wherein the tissue interface surface has a curved shape.

10. The apparatus of claim 7, wherein the tissue interface surface is conformable.

11. The apparatus of claim 10, wherein the tissue interface surface is conformable to a skin surface.

12. The apparatus of claim 1, wherein the dielectric electrode has a resistance that varies with a temperature.

13. The apparatus of claim 12, wherein the temperature is one of a temperature of a tissue interface surface or a tissue positioned adjacent to the tissue interface.

14. The apparatus of claim 1, further comprising:
a power source coupled to the dielectric electrode.

15. The apparatus of claim 14, further comprising:
feedback control resources coupled to at least one of the power source, the dielectric electrode or the sensor.

16. The apparatus of claim 15, wherein the feedback control resources include at least one of a microprocessor, a controller, a software program set forth in a tangible media, a power control circuit or a voltage and current monitor.

17. The apparatus of claim 1, wherein the RF electrode is a monopolar electrode.

18. The apparatus of claim 17, further comprising:
an RE power supply electronically coupled to e RF electrode; and
a ground pad electrode positioned on the skin and coupled to the RF power source and the RF electrode.

19. The apparatus of claim 1, wherein the RF electrode is a bipolar electrode and includes one of a plurality of electrodes, a plurality of multiplexed electrodes, an array of electrodes or an array of multiplexed electrodes.

20. The apparatus of claim 1, further comprising:
a switching device, wherein the RF electrode includes a plurality of RF electrodes coupled to the switching device.

21. The apparatus of claim 20, wherein the switching device includes one of a multiplexing device or a multiplexing device configured to be coupled to an RF power source.

22. An apparatus for treating to skin, comprising:
a handpiece; and
a dielectric electrode coupled to the handpiece and including at least One RF electrode with a front surface and a back surface that is physically and electrically coupled to a back surface of a dielectric, at least a portion of the dielectric configured to contact a skin surface; and
a sensor coupled to the dielectric electrode.

23. The apparatus of claim 22, wherein the dielectric electrode is configured to be capacitively coupled to the skin.

24. The apparatus of claim 22, wherein the RF electrode is a monopolar electrode.

25. The apparatus of claim 22 further comprising:
an RF power supply electronically coupled to the RF electrode; and
a ground pad electrode positioned on the skin and electronically coupled to the RF power source and the R electrode.

26. The apparatus of claim 22, wherein the RF electrode is a bipolar electrode and comprises one of a plurality of electrodes, a plurality of multiplexed electrodes, an array of electrodes or an array of multiplexed electrodes.

27. The apparatus of claim 26, further comprising:
a switching device coupled to at least a portion of the plurality of RF electrodes, the switching device configured to be coupled to at least one of a power supply or feedback control resources.

28. The apparatus of claim 27, wherein the switching device includes one of a multiplexing device or a multiplexing device coupled to an RF power source.

29. The apparatus of claim 22, wherein the dielectric electrode comprises a plurality of dielectric portions including a first portion and second portion.

30. The apparatus of claim 29, wherein the first and second portions are substantially positioned on an energy delivery device surface.

31. The apparatus of claim 30, wherein the first portion is positioned within an interior area defined by the second portion.

32. The apparatus of claim 31, further comprising:
a gap disposed between the first portion and the second portion.

33. The apparatus of claim 31, wherein the first and second portions have one of a substantially circular shape or an oval shape.

34. The apparatus of claim 33, wherein the first and second portions are substantially concentric.

35. The apparatus of claim 29, further comprising:
a switching device coupled to at least one of the plurality of dielectric portions.

36. The apparatus of claim 35, wherein the switching device includes one of a multiplexing device or a multiplexing device coupled to an RF power source.

37. An apparatus for treating the skin, comprising:
a handpiece; and
an energy delivery device coupled to tie handpiece, the energy delivery device having a conductive portion and a dielectric portion, the energy delivery device configured to be coupled to a power source, at least a portion of the dielectric portion configured to contact a skin surface;
a cooling media delivery member coupled to the energy delivery device; and
a sensor coupled to one of the energy delivery device, the energy delivery device, the tissue interface surface or a power source coupled to the energy delivery device.

38. The apparatus of claim 37, further comprising:
a pressure relief valve coupled to the energy delivery device.

39. The apparatus of claim 37, wherein the energy delivery device is configured to reduce at least one of an edge effect, an electrode edge effect, an electrode temperature gradient, an electrode current density gradient or a tissue interface surface temperature gradient.

40. The apparatus of claim 37, wherein the conductive portion is a conductive layer and the dielectric portion is a dielectric layer.

41. The apparatus of claim 40, wherein the conductive portion has a surface area that is less than a dielectric layer surface area.

42. The apparatus of claim 40, wherein the energy delivery device is configured such that substantially all of an energy delivery device current flows through the conductive layer.

43. The apparatus of claim 40, wherein the dielectric layer is a tissue contacting layer and the conductive layer is disposed on a non-tissue contacting side of the dielectric layer.

44. The apparatus of claim 40, wherein the dielectric layer is one of an oxide layer, a metal oxide layer, a polymer, a polyimide or a diamond.

45. The apparatus of claim 40, wherein the dielectric layer has a thickness of about 0.001 inches.

46. The apparatus of claim 40, wherein the conductive layer is one of a metal, a metal alloy, copper or a conductive polymer.

47. The apparatus of claim 31, wherein the cooling media delivery member delivers a cooling media to the energy delivery device and cool at least a portion of the energy delivery device by at least one of a conductive effect, an evaporative effect, a convective effect or an ebullient cooling effect.

48. The apparatus of claim 37, further comprising:
   a source of cooling media coupled to at cooling media delivery member, the cooling media delivery member including at least one of a flow control device and a control valve or a nozzle.

49. The apparatus of claim 48, wherein the cooling media is one of a cooling fluid, a gas, a cryogenic gas, a liquid, an electrolytic solution, a cooled liquid or a cryogenic liquid.

50. The apparatus of claim 37, wherein at least a portion of the energy delivery device is flexible or elastic.

51. The apparatus of claim 50, wherein the energy delivery device is one of a membrane, a flexible membrane, a skin conforming membrane, a film, a flexible film or a skin conforming film.

52. The apparatus of claim 50, wherein the at least a portion of the energy delivery device is deformable in response to a pressure.

53. The apparatus of claim 52, further comprising:
   a valve coupled to the handpiece, wherein the valve is one of a control valve, a pressure valve or a pressure relief valve.

54. The apparatus of claim 53, further comprising:
   feedback control resources coupled to at least one of the valve or the sensor.

55. The apparatus of claim 37, wherein the conductive portion is an RF electrode.

56. The apparatus of claim 55, wherein the RF electrode is a monopolar electrode.

57. The apparatus of claim 56 further comprising,
   an RF power supply electronically coupled to the RF electrode; and
   a ground pad electrode positioned on the skin and electronically coupled to the RF power source and the RF electrode.

58. The apparatus of claim 55, wherein the RF electrode is a bipolar electrode and comprises one of a plurality of electrodes, a plurality of multiplexed electrodes, an array of electrodes or an array of multiplexed electrodes.

59. The apparatus of claim 58, further comprising:
   a switching device coupled to at least a portion of the plurality of RF electrodes, the switching device configured to be coupled to at least one of a power supply or feedback control resources.

60. The apparatus of claim 59, wherein the switching device includes one of a multiplexing device or a multiplexing device coupled to an RF power source.

* * * * *

UNITED STATES PATENT AND TRADEMARK OFFICE
CERTIFICATE OF CORRECTION

PATENT NO. : 6,413,255 B1
APPLICATION NO. : 09/522275
DATED : July 2, 2002
INVENTOR(S) : Roger A. Stern It is certified that error appears in the above-identified patent and that said Letters Patent is hereby corrected as shown below:

Column 30:

In claim 1, line 4, change "RE" to --RF--.

In claim 1, line 8, insert a carriage return after the ";" and before "a".

In claim 3, line 3, before the word "voltage" insert --a--.

In claim 4, line 3, change "delively" to --delivery--.

Column 31

In claim 18, line 2, change "RE" to --RF--, and change "e" to --the--.

In claim 22, line 4, change "One" to --one--.

In claim 25, line 5, change "R" to --RF--.

Column 32

In claim 37, line 2, after ";" delete --and--.

In claim 37, line 3, change "tie" to --the--.

In claim 37, line 11, after "of" delete the first occurrence of "the energy delivery device,".

UNITED STATES PATENT AND TRADEMARK OFFICE
CERTIFICATE OF CORRECTION

PATENT NO. : 6,413,255 B1
APPLICATION NO. : 09/522275
DATED : July 2, 2002
INVENTOR(S) : Roger A. Stern It is certified that error appears in the above-identified patent and that said Letters Patent is hereby corrected as shown below:

Column 33:

In claim 47, line 1, change "31" to --37--.

In claim 47, line 3, change "cool" to --cools--.

In claim 48, line 2, change "at" to --the--.

Signed and Sealed this

Tenth Day of October, 2006

JON W. DUDAS
*Director of the United States Patent and Trademark Office*